United States Patent [19]
Bender et al.

[11] Patent Number: 5,985,900
[45] Date of Patent: Nov. 16, 1999

[54] METALLOPROTEINASE INHIBITORS, PHARMACEUTICAL COMPOSITIONS CONTAINING THEM AND THEIR PHARMACEUTICAL USES

[75] Inventors: Steven L. Bender, Oceanside; Melwyn A. Abreo, Imperial Beach, both of Calif.

[73] Assignee: Agouron Pharmaceuticals, Inc., La Jolla, Calif.

[21] Appl. No.: 09/049,949

[22] Filed: Mar. 30, 1998

Related U.S. Application Data

[60] Provisional application No. 60/041,821, Apr. 1, 1997.
[51] Int. Cl.$^6$ .......................... A01N 43/40; A01N 43/80; A01N 43/50; A01N 37/28
[52] U.S. Cl. .......................... 514/336; 514/340; 514/351; 514/357; 514/378; 514/400; 514/507; 514/518; 514/562; 546/272.1; 546/283.4; 546/293; 546/335; 548/247; 548/339.5; 548/338.1; 560/12; 562/430; 562/623
[58] Field of Search .................................... 514/336, 340, 514/351, 357, 378, 400, 507, 518, 562; 546/272.1, 283.4, 293, 335; 548/247, 339.5, 338.1; 560/12; 562/430, 623

[56] References Cited

U.S. PATENT DOCUMENTS

| | | | |
|---|---|---|---|
| 4,032,639 | 6/1977 | Freed et al. | 424/251 |
| 5,183,900 | 2/1993 | Galardy et al. | 548/495 |
| 5,189,178 | 2/1993 | Galardy et al. | 548/495 |
| 5,256,657 | 10/1993 | Singh et al. | 514/228.2 |
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |
| 5,569,665 | 10/1996 | Porter et al. | 514/357 |

FOREIGN PATENT DOCUMENTS

| | | |
|---|---|---|
| 276 436 A1 | 8/1988 | European Pat. Off. . |
| 438 223 A1 | 8/1991 | European Pat. Off. . |
| 0 489 577 A1 | 6/1992 | European Pat. Off. . |
| 0 489 579 A1 | 6/1992 | European Pat. Off. . |
| 0 606 046 A1 | 7/1994 | European Pat. Off. . |
| 0 757 037 A2 | 2/1997 | European Pat. Off. . |
| 0 757 984 A1 | 2/1997 | European Pat. Off. . |
| 0780 386 A1 | 6/1997 | European Pat. Off. ...... C07D 309/08 |
| 195 42 189 A1 | 5/1997 | Germany . |
| WO 92/06966 | 4/1992 | WIPO . |
| WO 92/09563 | 6/1992 | WIPO . |
| WO 92/21360 | 12/1992 | WIPO . |
| WO 93/24449 | 12/1993 | WIPO . |
| WO 93/24475 | 12/1993 | WIPO . |
| WO 94/02466 | 2/1994 | WIPO . |
| WO 94/12169 | 6/1994 | WIPO . |
| WO 94/24140 | 10/1994 | WIPO . |
| WO 94/25434 | 11/1994 | WIPO . |
| WO 95/04735 | 2/1995 | WIPO . |
| WO 95/12603 | 5/1995 | WIPO . |
| WO 95/19961 | 7/1995 | WIPO . |
| WO 95/22966 | 8/1995 | WIPO . |
| WO 95/32944 | 12/1995 | WIPO . |
| WO 95/35275 | 12/1995 | WIPO . |
| WO 95/35276 | 12/1995 | WIPO . |
| WO 96/00214 | 1/1996 | WIPO . |
| WO 96/06074 | 2/1996 | WIPO . |
| WO 96/16027 | 5/1996 | WIPO . |
| WO 96/16931 | 6/1996 | WIPO . |
| WO 96/23791 | 8/1996 | WIPO . |
| WO 96/27583 | 9/1996 | WIPO . |

(List continued on next page.)

OTHER PUBLICATIONS

Database CAPLUS on STN, Acc. No. 1979:152610, Okamoto et al., 'N2–Arylsulfonyl–L–argininamides.' DE 2801478 A1 (abstract), 1979.

Robinson, et al., "Inhibitors of MMP–1: An Examination of P1' $C_\alpha$ Gen–Disubsitution in the Succinamide Hydroxamate Series," *Bioorganic & Medicinal Chemistry Letters*, vol. 6, No. 14 (1996), pp. 1719–1724.

Firestone, et al., "Total Synthesis of β–Lactam Antibiotics. IV. Epimerization of 6(7)–Aminopenicillins and–cephalosporins from α to β$^1$," *Journal of Organic Chemistry*, vol. 39, No. 4 (1974), pp. 437–440.

Walker, "Vinylogous Amides of 2–Methylaminoethanol and Their Behavior with Lithium Aluminum Hydride. Vinylogous Urethanes of Ethanolamides and Their Acetylation," *Journal of Organic Chemistry*, vol. 27 (1962), pp. 4227–4231.

(List continued on next page.)

*Primary Examiner*—Gary Geist
*Assistant Examiner*—Brian J. Davis

[57] ABSTRACT

Compounds of the formula I:

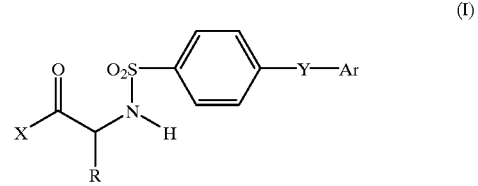

wherein Y is O or S, Ar is an aryl group or a heteroaryl group, R is H, an alkyl group, a cycloalkyl group, a heterocycloalkyl group, an aryl group, a heteroaryl group, or —C(O)$R_1$, wherein $R_1$ is hydrogen, an alkyl group, a cycloalkyl group, a heterocycloalkyl group, an aryl group, a heteroaryl group, or $NR_2R_3$, wherein $R_2$ and $R_3$ independently are hydrogen, an alkyl group, a cycloalkyl group, a heterocycloalkyl group, an aryl group, or a heteroaryl group, and X is —NH—OH or —OH. Pharmaceutically acceptable prodrugs, salts and solvates of these compounds. Methods of inhibiting the activity of metalloproteinases by administering a compound of the formula I or a prodrug, salt of solvate thereof. Pharmaceutical compositions comprising an effective amount of these compounds, prodrugs, salts, and solvates.

24 Claims, No Drawings

FOREIGN PATENT DOCUMENTS

| | | |
|---|---|---|
| WO 96/33172 | 10/1996 | WIPO . |
| WO 97/18194 | 5/1997 | WIPO . |
| WO 97/19068 | 5/1997 | WIPO . |
| WO 97/20824 | 6/1997 | WIPO . |
| WO 97/22587 | 6/1997 | WIPO . |
| WO 97/23459 | 7/1997 | WIPO . |
| WO 97/25969 | 7/1997 | WIPO . |
| WO 97/27174 | 7/1997 | WIPO . |
| WO 98/07697 | 2/1998 | WIPO . |
| WO 98/08815 | 3/1998 | WIPO . |
| WO 98/08825 | 3/1998 | WIPO . |

OTHER PUBLICATIONS

Cumberbatch, et al., "The Synthesis and Conformational Analysis of a Pair of Diastereoisomeric Cyclic Peptides with cis and trans Amide Bonds, Respectively," *Journal of the Chemical Society, Chemical Communications,* No. 7 (1993), pp. 641–642.

Capps, et al., "Novel Catalytic Rearrangements of 2–Vinyl–1,3–Thiazetidines," *Tetrahedron Letters,* vol. 25, No. 37 (1984), pp. 4157–4160.

Sakai, et al., "Convenient Synthesis of 1,4–Thiazane–3–Carboxylic Acid Derivatives," *Chemical and Pharmaceutical Bulletin,* vol. 29, No. 6 (1981), pp. 1554–1560.

Woessner, Jr., "Matrix Metalloproteinases and their Inhibitors in Connective Tissue Remodeling", *The FASEB Journal,* vol. 5, No. 8 (1991), pp. 2145–2154.

Freije et al., "Molecular Cloning and Expression of Collagenase–3, a Novel Human Matrix Metalloproteinase Produced by Breast Carcinomas", *The Journal of Biological Chemistry,* vol. 269, No. 24 (1994), pp. 16766–16773.

Mitchell et al., "Cloning, Expression, and Type II Collagenolytic Activity of Matrix Metalloproteinase–13 from Human Osteoarthritic Cartilage", *The Journal of Clinical Investigation,* vol. 97, No. 3 (1996), pp. 761–768.

Ray et al., "Matrix Metalloproteinases and Malignant Disease: Recent Developments", *Expert Opinion on Investigational Drugs,* vol. 5, No. 3 (1996), pp. 323–335.

Birkedal–Hansen, "Host–Mediated Extracellular Matrix Destruction by Metalloproteinases", *Molecular Pathogenesis of Periodontal Disease* (1994), pp. 191–202.

Gijbels et al., "Gelatinase in the cerebrospinal fluid of patients with multiple sclerosis and other inflammatory neurological disorders", *Journal of Neuroimmunology,* 41 (1992), pp. 29–34.

O'Day et al., "Differences in Response in Vivo to Amphotericin B Among *Candida albicans* Strains", *Investigative Ophthalmology & Visual Science,* vol. 32, No. 5 (1991), pp. 1569–1572.

Rosenberg et al., "Tumor Necrosis Factor–α–Induced Gelatinase B Causes Delayed Opening of the Blood–Brain Barrier: An Expanded Therapeutic Window", *Brain Research,* vol. 703, Nos. 1–2 (1995), pp. 151–155.

Rosenberg et al., "Proteolytic Cascade Enzymes Increase in Focal Cerebral Ischemia in Rat", *Journal of Cerebral Blood Flow and Metabolism,* vol. 16, No. 3 (1996), pp. 360–366.

Fisher et al., "Molecular Basis of Sun–Induced Premature Skin Ageing and Rretinoid Aantagonism", *Nature,* vol. 379, No. 6563 (1996), pp. 335–339.

Saarialho–Kere et al., "Distinct Populations of Basal Keratinocytes Express Stromelysin–1 and Stromelysin–2 in Chronic Wounds", *The Journal of Clinical Investigation,* vol. 94 (1994), pp. 79–88.

Newby et al., "Extracellular Mmatrix Ddegrading Mmetalloproteinases in the Ppathogenesis of Aarteriosclerosis", *Arteriosclerosis,* Supplement to Basic Research in Cardiology, vol. 89, Supl. 1 (1994), pp. 59–70.

McMillan et al., "Characterization of a Glomerular Epithelial Cell Metalloproteinase as Matrix Metalloproteinase–9 with Enhanced Expression in a Model of Membranous Nephropathy", *The Journal of Clinical Investigation,* vol. 97, No. 4 (1996), pp. 1094–1101.

Belaaouaj et al., "Human Macrophage Metalloelastase", *The Journal of Biological Chemistry,* vol. 270, No. 24 (1995), pp. 14568–14575.

Martin, "Synthesis of Aldehydes, Ketones, and Carboxylic Acids from Lower Carbonyl Compounds by C–C Coupling Reactions", *Synthesis,* No. 9 (1979), pp. 633–655.

Yabroff et al., "The Relative Strengths of Some Hydrocarbon Derivatives of Boric Acid", *The Journal of the American Chemical Society,* vol. 56 (1934), pp. 1850–1857.

Malon et al., "Chiroptical Properties and Conformation of N–Acetyl–L–Amino Acids N'–Methylamides with Aliphatic Side Chains", *Collection Czechoslovak Chem. Commun.,* vol. 48 (1983), pp. 2844–2861.

Pridgen et al., "Regiospecific Synthesis of Arylfurans Employing a Nickel(II)–Phosphine Complex as a Catalyst in the Homolytic Cross–Coupling of Grignard Reagents to Halofurans", *J. Org. Chem.,* vol. 47, No. 8 (1982), pp. 1590–1592.

Yang et al., "Regiospecific Synthesis of 3,4–Disubstituted Furans and 3–Substituted Furans Using 3,4–Bis(tri–n–butylstannyl)furan and 3–(Tri–n–butylstannyl)furan as Building Blocks", *Tetrahedron,* vol. 50, No. 32 (1994), pp. 9583–9608.

Ribereau et al., "Synthesis and Physical Properties of the Six Furylpyridines", *Canadian Journal of Chemistry,* vol. 61, No. 2 (1983), pp. 334–342.

Ishikura et al., "A Novel Synthesis of 4–Aryl– and 4–Heteroarylpyridines via Diethyl(4–pyridyl)borane", *Chem. Pharm. Bull.,* vol. 33, No. 11 (1985), pp. 4755–4763.

Delacotte et al., "Synthesis of Tritiated Threonine with a High Specific Activity", *Journal of Labelled Compounds and Radiopharmaceuticals,* vol. 29, No. 10 (1991), pp. 1141–1146.

Friedrich–Bochnitschek et al., "Allyl Esters as Carboxy Protecting Groups in the Synthesis of O–Glycopeptides", *J. Org. Chem.* (1989) vol. 54, pp. 751–756.

Belshaw et al., "Chlorotrimethylsilane Mediated Formation of ω–Allyl Esters of Aspartic and Glutamic Acids", *Synthetic Communications,* vol. 20, No. 20 (1990), pp. 3157–3160.

McNamara et al., "Synthesis of 4–Cyano–4'–halobiphenyls", *J. Org. Chem.,* vol. 41, No. 6 (1976), p. 1071.

Amatore et al., "Efficient Palladium–Catalyzed Synthesis of Unsymmetrical Donor–Acceptor Biaryls and Polyaryls", *Journal of Organometallic Chemistry,* vol. 390, No. 3 (1990), pp. 389–398.

Boy et al., "Electrosynthesis of Unsymmetrical Donor–Acceptor Polyaryls", *Tetrahedron Letters,* vol. 33, No. 4 (1992), pp. 491–494.

Pospíšek et al., "Tert–Leucine and Its Simple Peptides", *Collection Czechoslov. Chem. Commun.,* vol. 42 (1977), pp. 1069–1076.

Carpino et al., "Tetramethylfluoroformamidinium Hexafluorophosphate: A Rapid–Acting Peptide Coupling Reagent for Solution and Solid Phase Peptide Synthesis", *J. Am. Chem. Soc.,* vol. 117, No. 19 (1995), pp. 5401–5402.

Freskos, "Use of R–Pantolactone in the Synthesis of L–Tert Leucine Derivatives", *Synthetic Communications,* vol. 24, No. 4 (1994), pp. 557–563.

Abdel–Meguid et al., "An Orally Bioavailable HIV–1 Protease Inhibitor Containing an Imidazole–Derived Peptide Bond Replacement: Crystallographic and Pharmacokinetic Analysis", *Biochemistry,* vol. 33, No. 39 (1994), pp. 11671–11677.

Mathias, "Esterification and Alkylation Reactions Employing Isoureas", *International Journal of Methods in Synthetic Organic Chemistry,* No. 8 (1979), pp. 561–576.

Boger et al., "Total Synthesis of Azafluoranthene Alkaloids: Rufescine and Imeluteine", *J. Org. Chem.* (1984), vol. 49, No. 21, pp. 4050–4055.

Ellis et al., "Antifungal Activity of some Imidazole Derivatives", *J. Pharm. Pharmacol.* (1964), vol. 16, pp. 400–407.

Von E. Felder et al., Helv. Chim. Acta, vol. 43, No. 117 (1960), p. 888–894.

Aebischer et al., "Synthesis and NMDA Antagonistic Properties of the Enantiomers of 4–(3–Phosphonopropyl)piperazine–2–carboxylic Acid (CPP) and of the Unsaturated Analogue (E)–4(3–Phosphonoprop–2–enyl)piperazine–2–carboxylic Acid (CPP–ene)," Helvetica Chimica Acta, vol. 72 (1989), p. 1043–1051.

Brunwin et al., "Total Synthesis of Nuclear Analogues of 7–Methylcephalosporin," *J.C.S. Perkin I Transactions* (1973), p. 1321–1328.

Knight et al., "A Novel Coumarin–Labelled Peptide for Sensitive Continuous Assays of the Matrix Metalloproteinases," FEBS, vol. 296, No. 3 (1992), p. 263–266.

Menegatti et al., "Inhibition of Serine Proteinases by Tetra–p–Amidinophenoxy–neo–Pentane: Thermodynamic and Molecular Modeling Study," *J. Enzyme Inhibition,* vol. 2 (1987), p. 23–30.

Johnson, "Collagenase Inhibitors," *Drug News and Perspectives,* vol. 3, No. 8 (1990), p. 453–458.

Henderson et al., "Design of Inhibitors of Articular Cartilage Destruction," Drugs of the Future, vol. 15, No. 5 (1990), p. 495–508.

Harrison et al., "A Semicontinuous, High–Performance Liquid Chromatography–Based Assay for Stromelysin," *Analytical Biochemistry,* vol. 180 (1989), p. 110–113.

Shinmei et al., "The Mechanism of Cartilage Degradation in Osteoarthritic Joints," Seminars in Arthritis and Rheumatism, vol. 19, No. 4, Suppl. 1 (1990), p. 16–20.

Weingarten et al., "Spectrophotometric Assay for Vertebrate Collegenase," *Analytical Biochemistry,* vol. 147 (1985) p. 437–440.

Davies et al., "A Synthetic Matrix Metalloproteinase Inhibitor Decreases Tumor Burden and Prolongs Survival of Mice Bearing Human Ovarian Carcinoma Xenografts," *Cancer Research,* vol. 53 (1993), p. 2087–2091.

Brinckerhoff, "Joint Destruction in Arthritis: Metalloproteinases in the Spotlight," *Arthritis & Rheumatism,* vol. 34, No. 9 (1991), p. 1073–1075.

Morrison, "Kinetics of the Reversible Inhibition of Enzyme–Catalysed Reactions by Tight–Binding Inhibitors," *Biochem. Biophys. Acta,* vol. 185 (1969), p. 269–286.

Lohmander et al., "Metalloproteinases, Tissue Inhibitor, and Proteoglycan Fragments in Knee Synovial Fluid in Human Osteoarthritis," *Arthritis & Rheumatism,* vol. 36, No. 2 (1993), p. 181–187.

Schwartz et al., "Synthetic Inhibitors of Bacterial and Mammalian Interstitial Collagenases," *Progress in Medicinal Chemistry,* vol. 29 (1992), p. 271–334.

Johnson et al., "Collagenase Inhibitors: Their Design and Potential Therapeutic Use", *J. Enzyme Inhibition,* vol. 2, (1987), p. 1–22.

Morphy et al., "Matrix Metalloproteinase Inhibitors: Current Status," *Current Medicinal Chemistry,* (1995), vol. 2, pp. 743–762.

Porter et al., "Recent Developments in Matrix Metalloproteinase Inhibitors," *Exp. Opin. Ther. Patents* (1995) vol. 5, No. 12, pp. 1287–1296.

Beckett et al., "Recent advances in matrix metalloproteinase inhibitor research," *Drug Discovery Today,* vol. 1, No. 1 (Jan. 1996), pp. 16–26.

Greenstein et al., *Chemistry of the Amino Acids,* (1984), vol. 2, p. 886–889.

Smith et al., "A Superior Synthesis of Diaryl Ethers by the Use of Ultrasound in the Ullmann Reaction," *J. Chem. Soc. Perkin Trans. I,* (1992), p. 407–408.

Sammes et al., "A Novel, Simple Method for the Preparation of Hindered Diphenyl Ethers," *J. Chem. Soc. Perkin Trans. I,* (1988), p. 3229–3231.

Hassner et al., "Aminopyridines as Acylation Catalysts for Tertiary Alcohols," *Tetrahedron,* vol. 34 (1978), pp. 2069–2076.

Sprague et al., "Studies in the Cyanine Dye Series. IX. 4,4'–Pyridocyanines and 4–Pyrido–4'–cyanines," *Journal of the American Chemical Society,* vo. 59, No. 12 (1937), p. 2697–2699.

Shao et al., "An Enantiomeric Synthesis of allo–Threonines and β–Hydroxyvalines," *J. Org. Chem.,* vol. 61, No. 8 (1996), pp. 2582–2583.

Thompson et al., "A General Synthesis of 5–Arylnicotinates," *J. Org. Chem.,* vol. 49, No. 26 (1984), pp. 5237–5243.

Gehring et al., "Characterization of the Phe–81 and Val–82 Human Fibroblast Collagenase Catalytic Domain Purified from *Escherichia coli,"* The Journal of Biological Chemistry, vol. 270, No. 38 (1995), pp. 22507–22513.

Marcy et al., "Human Fibroblast Stromelysin Catalytic Domain: Expression, Purification, and Characterization of a C–Terminally Truncated Form," *Biochemistry,* vol. 30, No. 26 (1991), p. 6476–6483.

Tamura et al., "Highly Selective and Orally Active Inhibitors of Type IV Collagenase (MMP–9 and MMP–2): N–Sulfonylamino Acid Derivatives", J. Med. Chem. (1998), 41(4), pp. 640–649.

METALLOPROTEINASE INHIBITORS, PHARMACEUTICAL COMPOSITIONS CONTAINING THEM AND THEIR PHARMACEUTICAL USES

RELATED APPLICATION DATA

This application claims priority benefits under 35 U.S.C. § 119 based on U.S. Provisional Patent Application No. 60/041,821, filed Apr. 1, 1997, which application is entirely incorporated herein by reference.

DESCRIPTION OF THE INVENTION

The present invention relates to compounds that inhibit metalloproteinases, particularly matrix metalloproteinases and tumor necrosis factor-α convertase, and their pharmaceutically acceptable salts and pharmaceutically acceptable prodrugs. The invention further relates to the uses of these compounds, salts and prodrugs for the therapeutic treatment of humans or animals.

Matrix metalloproteinases ("MMPs") are a family of enzymes, including, but not limited to, collagenases, gelatinases, matrilysin, and stromelysins, which are involved in the degradation and remodelling of connective tissues. These enzymes are found in a number of cell types that are found in or associated with connective tissue, such as fibroblasts, monocytes, macrophages, endothelial cells and metastatic tumor cells. They also share a number of properties, including zinc and calcium dependence, secretion as zymogens, and 40–50% amino acid sequence homology.

Matrix metalloproteinases degrade the protein components of the extracellular matrix, i.e. the protein components found in the linings of joints, interstitial connective tissue, basement membranes, cartilage and the like. These proteins include collagen, proteoglycan, fibronectin and lamanin.

Collagen is the major structural protein of mammalian tissue, comprising one-third of the total protein in mammalian organisms, and is an essential component of many matrix tissues, including cartilage, bone, tendons and skin. Interstitial collagenases catalyze the initial (rate-limiting) cleavage of native collagen types I, II, III and X. These enzymes cleave collagen into two fragments which spontaneously denature at physiological temperature. Denaturation of collagen involves conversion of the rigidly coiled helix to a random coil referred to as gelatin. These gelatin (denatured collagen) fragments are then subject to further cleavage and degradation by less specific enzymes. The net result of collagenase cleavage is thus the loss of structural integrity in the matrix tissue (collagen collapse), an essentially irreversible process.

The gelatinases include two distinct yet highly related enzymes: a 72-kiloDalton (kDa) enzyme and a 92-kiloDalton enzyme. The former is released by fibroblasts while the latter is released by mononuclear phagocytes, neutrophils, corneal epithelial cells, tumor cells, cytotrophoblasts and keratinocytes. Both enzymes degrade gelatins (denatured collagens), collagen types IV (basement membrane) and V, fibronectins (high molecular weight multifunctional glycoproteins found in soft connective tissue and basement membranes) and insoluble elastin (highly cross-linked hydrophobic proteins found in load bearing fibers of mammalian connective tissue).

Stromelysins (1 and 2) cleave a broad range of matrix substrates, including lamanin, fibronectins, proteoglycans and collagen types IV and IX (non-helical).

Matrilysin (putative metalloproteinase or PUMP) also degrades a wide variety of matrix substrates, including proteoglycans, gelatins, fibronectins, elastins and lamanin. Matrilysin has been found in mononuclear phagocytes, rat uterine explants and tumor cells.

In normal tissues, the activity of matrix metalloproteinases is tightly regulated. As a result, the breakdown of connective tissue mediated by these enzymes is generally in a dynamic equilibrium with synthesis of new matrix tissue.

In a number of pathological disease conditions, however, deregulation of matrix metalloproteinase activity leads to the uncontrolled breakdown of extracellular matrix. These disease conditions include arthritis (e.g., rheumatoid arthritis and osteoarthritis), periodontal disease, aberrant angiogenesis, tumor metastasis and invasion, tissue ulceration (e.g., corneal ulceration, gastric ulceration or epidermal ulceration), bone disease, HIV-infection and complications from diabetes.

Administration of matrix metalloproteinase inhibitors has been found to reduce the rate of connective tissue degradation, thereby leading to a favorable therapeutic effect. For example, in *Cancer Res.*, vol. 53, p. 2087 (1993), a synthetic matrix metalloproteinase inhibitor was shown to have in vivo efficacy in a murine model for ovarian cancer with an apparent mode of action consistent with inhibition of matrix remodelling. The design and uses of MMP inhibitors are reviewed, for example, in *J. Enzyme Inhibition*, 2, 1–22 (1987); *Progress in Medicinal Chemistry* 29, 271–334 (1992); *Current Medicinal Chemistry*, 2, 743–762 (1995); *Exp. Opin. Ther. Patents*, 5,1287–1296 (1995); and *Drug Discovery Today*, 1, 16–26 (1996).

Matrix metalloproteinase inhibitors are also the subject of numerous patents and patent applications, including: U.S. Pat. No. 5,189,178; U.S. Pat. No. 5,183,900; U.S. Pat. No. 5,506,242; U.S. Pat. No. 5,552,419; U.S. Pat. No. 5,455,258; European Patent Application No. 0 438 223; European Patent Application No. 0 276 436; WIPO International Publication No. WO 92/21360; WIPO International Publication No. WO 92/06966; WIPO International Publication No. WO 92/09563; WIPO International Publication No. WO 96/00214; WIPO International Publication No. 95/35276; WIPO International Publication No. WO 96/27583, and WIPO International Publication No. WO 96/33172, the disclosures of each of which are incorporated herein by reference.

Tumor necrosis factor- ("TNF-α") is a cytokine which is produced as a 28-kDa precursor and released in an active 17-kDa form. This active form can mediate a large number of deleterious effects in vivo, including inflammation, fever, cardiovascular effects, haemorrhage, coagulation and acute phase responses, similar to those seen during acute infections and shock states. Chronic administration of TNF-α can cause cachexia and anorexia; accumulation of excess of TNF-α can be fatal.

TNF-α convertase is a metalloproteinase involved in the biosynthesis of TNF-α. Inhibition of TNF-α convertase inhibits production of TNF-α.

Since excessive TNF-α production has been noted in several disease conditions characterized by MMP-mediated tissue degradation, including multiple sclerosis, arthritis and cancer, compounds which inhibit both MMPs and TNF-α convertase are especially advantageous for the treatment or prophylaxis of disease conditions in which both mechanisms are involved. Although compounds that both inhibit MMPs activity and TNF-α production have been disclosed in WIPO International Publication Nos. WO 94/24140 and WO 94/02466, the disclosures of which are herein incorporated by reference, there is still a need for effective MMP and/or TNF-α convertase inhibiting agents.

Because of their beneficial therapeutic effects, there is a need for effective inhibitors of metalloproteinase activity. The present invention is therefore directed to certain compounds that inhibit metalloproteinases, such as MMPs and TNF-α convertase, their pharmaceutically acceptable prodrugs, salts and solvates, pharmaceutical compositions containing the same and methods of using the same, as well as to method and intermediates useful in their preparation. Additional features and advantages of the invention will be set forth in the description which follows, and in part will be apparent from the description or may be learned from practice of the invention.

To achieve these and other advantages, the present invention provides a compound of formula I:

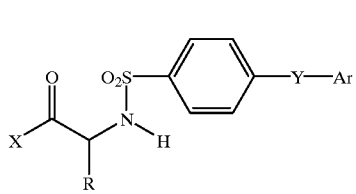

(I)

wherein Y is O or S; Ar is an aryl group or a heteroaryl group; R is H, an alkyl group, a cycloalkyl group, a heterocycloalkyl group, an aryl group, a heteroaryl group, or —C(O)R$_1$, wherein R$_1$ is hydrogen, an alkyl group, a cycloalkyl group, a heterocycloalkyl group, an aryl group, a heteroaryl group, or NR$_2$R$_3$, wherein R$_2$ and R$_3$ independently are hydrogen, an alkyl group, a cycloalkyl group, a heterocycloalkyl group, an aryl group, or a heteroaryl group; and X is —NH—OH or —OH, or a pharmaceutically acceptable prodrug, salt or solvate thereof.

The present invention is also directed to a pharmaceutical composition comprising (a) a therapeutically effective amount of a compound as defined in claim 1 or a pharmaceutically acceptable prodrug, salt or solvate thereof; and (b) a pharmaceutically acceptable carrier, diluent, vehicle or excipient.

The present invention is further directed to a method of treating a mammalian disease condition mediated by metalloproteinase activity which comprises administering to a mammal in need thereof a therapeutically effective amount of a compound of formula I or a pharmaceutically acceptable prodrug, salt or solvate thereof. More particulaly, the present invention is directed to a method of treating tumor growth, invasion or metastasis, osteoarthritis, rheumatoid arthritis, osteoporosis, periodontitis, gingivitis, chronic dermal wounds, corneal ulceration, degenerative skin disorders, multiple sclerosis, stroke, atherosclerosis, glomerular disease, Alzheimer's disease, or a disease condition characterized by unwanted angiogenesis, such as diabetic retinopathy, macular degeneration, angiofibromas, or hemangiomas.

The present invention is still further directed to a method of inhibiting the activity of a metalloproteinase that comprises contacting the metalloproteinase with an effective amount of a compound of formula (I) or a pharmaceutically acceptable prodrug, salt or solvate thereof.

As used in the present application, the following definitions apply, unless otherwise indicated:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below.

An "O-alkyl group" or "alkoxy group" is intended to mean an oxygen bonded to an alkyl group, wherein the alkyl group is as defined above.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, cyclopropyl, cyclobutyl, cyclopentyl, cyclopentenyl, cyclohexyl, cyclohexenyl, cycloheptyl, cyclooctyl, bicyclo[2.2.1.]heptyl, bicyclo[2.2.1.]hept-2-en-5-yl, bicyclo[2.2.2]octyl, bicyclo[3.2.1.]nonyl, bicyclo[4.3.0]nonyl, bicyclo[4.4.0]decyl, indan-1-yl, indan-2-yl, tetralin-1-yl, tetralin-2-yl, adamantyl, and the like.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1heptyl, 1,5,9-triazacyclododecyl, and the like.

An "aryl group" is intended to mean an aromatic, monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, fluoren-2-yl, indan-5-yl, and the like.

A "heteroaryl group" is intended to mean an aromatic monovalent monocyclic, bicyclic, ortricyciic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, pyrrolyl, imidazolyl, pyrazolyl, furyl, thienyl, thiazolyl, oxazolyl, isoxazolyl, isothiazolyl, oxadiazolyl, triazolyl, tetrazolyl, pyrazinyl, pyridyl, pyrimidyl, pyridazinyl, indolyl, isoindolyl, benzimidazolyl, benzofuryl, isobenzofuryl, benzothienyl, quinolyl, isoquinolyl, phthalazinyl, carbazolyl, purinyl, pteridinyl, acridinyl, phenanthrolinyl, phenoxazinyl, phenothiazinyl, and the like.

An "acyl group" is intended to mean a —C(O)—$R_5$— radical, wherein $R_5$ is any suitable substituent as defined below.

A "sulfonyl group" is intended to mean a —S(O)(O)—$R_5$— radical, wherein $R_5$ is any suitable substituent as defined below.

The term "suitable substituent" is intended to mean any of the substituents recognizable to those skilled in the art as not adversely affecting the inhibitory activity of the inventive compounds. Illustrative examples of suitable substituents include, but are not limited to, oxo groups, alkyl groups, hydroxy groups, halo groups, cyano groups, nitro groups, cycloalkyl groups, heterocycloalkyl groups, aryl groups, heteroaryl groups, trialkylsilyl groups,
groups of formula (A)

(A)

wherein $R_a$ is hydrogen, an alkyl group, a cycloalkyl group, a heterocycloalkyl group, an aryl group, or a heteroaryl group,
groups of formula (B)

(B)

wherein $R_a$ is hydrogen, an alkyl group, a cycloalkyl group, a heterocycloalkyl group, an aryl group, or a heteroaryl group,
groups of formula (C)

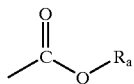

(C)

wherein $R_b$ and $R_c$ are independently hydrogen, an alkyl group, a cycloalkyl group, a heterocycloalkyl group, an aryl group, or a heteroaryl group,
groups of formula (D)

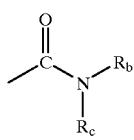

(D)

wherein $R_d$ is hydrogen, an alkyl group, a cycloalkyl group, a heterocycloalkyl group, an aryl group, a heteroaryl group, a hydroxy group, an alkoxy group, an amino group, an alkylamino group, a dialkylamino group, or an acylamino group; and $R_e$ is hydrogen, an alkyl group, a cycloalkyl group, a heterocycloalkyl group, an aryl group, a heteroaryl group, an amino group, an alkylamino group, or a dialkylamino group, groups of formula (E)

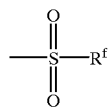

(E)

wherein $R_f$ is an alkyl group, a cycloalkyl group, a heterocycloalkyl group, an aryl group, or a heteroaryl group, groups of formula (F)

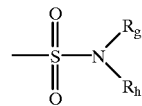

(F)

wherein $R_g$ and $R_h$ are independently hydrogen, an alkyl group, a cycloalkyl group, a heterocycloalkyl group, an aryl group, or a heteroaryl group, groups of formula (G)

(G)

wherein $R_i$ is an alkyl group, a cycloalkyl group, a heterocycloalkyl group, an aryl group, a heteroaryl group, or a group of formula (A), formula (B), formula (C), formula (H) (defined below), or formula (K) (defined below), groups of formula (H)

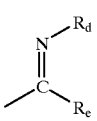

(H)

wherein $R_j$ is hydrogen, an alkyl group, a cycloalkyl group, a heterocycloalkyl group, an aryl group, a heteroaryl group, a hydroxy group, an alkoxy group, an amino group, or a group of formula (A), formula (B), formula (C) or formula (D); and wherein $R_k$ is hydrogen, an alkyl group, a cycloalkyl group, a heterocycloalkyl group, an aryl group, a heteroaryl group, or a group of formula (A), formula (B), formula (C), formula (D), formula (E), or formula (F), groups of formula (J)

(J)

wherein $R_l$ is hydrogen, an alkyl group, a cycloalkyl group, a heterocycloalkyl group, an aryl group, a heteroaryl group, or a group of formula (C), and
groups of formula (K)

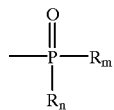
(K)

herein $R_m$ and $R_n$ are independently an alkyl group, a cycloalkyl group, a heterocycloalkyl group, an aryl group, a heteroaryl group, a hydroxy group, an alkoxy group, an amino group, an alkylamino group, or a dialkylamino group.

The term "suitable organic moiety" is intended to mean any organic moiety recognizable to those skilled in the art as not adversely affecting the inhibitory activity of the inventive compounds. Illustrative examples of suitable organic moieties include, but are not limited to oxo groups, alkyl groups, hydroxy groups, halo groups, cyano groups, nitro groups, cycloalkyl groups, heterocycloalkyl groups, aryl groups, heteroaryl groups, trialkylsilyl groups, and
groups of formulas (A), (B), (C), (D), (E), (F), (G), (H), (J), and (K), as defined above.

A "hydroxy group" is intended to mean the radical —OH.

An "oxo group" is intended to mean the divalent radical =O.

A "halo group" or is intended to mean any of the radicals —F, —Cl, —Br, or —I.

A "cyano group" is intended to mean the radical —C≡N.

A "nitro group" is intended to mean the radical —NO$_2$.

A "trialkylsilyl group" is intended to mean the radical —SiR$_p$R$_q$R$_s$, where $R_p$, $R_q$, and $R_s$ are each independently an alkyl group.

A "carboxy group" is intended to mean a group of formula (B) wherein $R_a$ is hydrogen.

A "alkoxycarbonyl group" is intended to mean a group of formula (B) wherein $R_a$ is an alkyl group as defined above.

A "carbamoyl group" is intended to mean a group of formula (C) wherein $R_b$ and $R_c$ are both hydrogen.

An "amino group" is intended to mean the radical —NH$_2$.

An "alkylamino group" is intended to mean the radical —NHR$_u$, wherein $R_u$ is an alkyl group as defined above.

A "dialkylamino group" is intended to mean the radical —NR$_u$R$_v$, wherein $R_u$ and $R_v$, which are the same or different, are each an alkyl group as defined above.

A "pharmaceutically acceptable prodrug" is intended to mean a compound that is converted under physiological conditions or by solvolysis to a compound of the formula I.

A "pharmaceutically acceptable solvate" is intended to mean a solvate that retains the biological effectiveness and properties of the biologically active components of compounds of formula I.

Examples of pharmaceutically acceptable solvates include, but are not limited to, compounds of formula I in combination with water, isopropanol, ethanol, methanol, DMSO, ethyl acetate, acetic acid, or ethanolamine.

In the case of solid formulations, it is understood that the inventive compounds may exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The inventive compounds may exist as single stereoisomers, racemates and/or mixtures of enantiomers and/or diastereomers. All such single stereoisomers, racemates and mixtures thereof are intended to be within the scope of the present invention. Preferably the inventive compounds, and prodrugs, salts and solvates thereof, have the formula Ia:

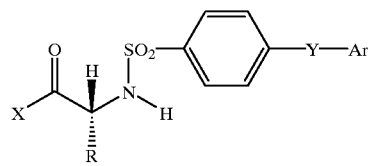
(Ia)

As generally understood by those skilled in the art, an optically pure compound having one chiralcenter (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

In the compounds, compositions and methods of the present invention, preferably Ar is an aryl group substituted with a suitable substitutent, as defined above, in the position para to the Y moiety. Preferably the suitable substituent is a halogen, an alkyl group, an O-alkyl group, an aryl group, a heteroaryl group, or an S-alkyl group.

Additionally it is preferred that R is an alkyl group, preferably the alkyl group —(CH$_3$)$_2$—S-alkyl, and still more preferably the alkyl group —C(CH$_3$)$_2$—S—CH$_2$-heteroaryl.

Particularly preferred compounds falling within formula I include:

2(S)—N-hydroxy-3,3-dimethyl-2-[(4-(4-fluorophenoxy) benzenesulfonyl)-amino]butanamide, 2(S)—N-hydroxy-3,3-dimethyl-2-[(4-(4-chlorophenoxy) benzenesulfonyl)-amino]butanamide, 2(S)—N-hydroxy-3-methyl-3-(pyrid-2-yl) methylsulfanyl-2-[(4-(4-fluorophenoxy) benzenesulfonyl)amino]butanamide, 2(S)—N-hydroxy-3-methyl-3-(pyrid-2-yl) methylsulfanyl-2-[(4-(4-bromophenoxy)- benzenesulfonyl)amino]butanamide, N-[4-(4-Bromophenoxy)benzenesulfonyl]—S—[(1-benzyl-1H-imidazol-2-yl)methyl]-D-penicillamine, N-[4-(4-Iodophenoxy)benzenesulfonyl]—S—[(pyrid-2-yl)methyl]-D-penicillamine, 2(S)—N-hydroxy-3-methyl-3-(pyrid-2-yl) methylsulfanyl-2-[(4-(4-iodophenoxy) benzenesulfonyl)amino]butanamide, N—[4-(4-Bromophenoxy)benzenesulfonyl]—S—[(5-methylisoxazol-3-yl)methyl]-D-penicillamine, 2(S)—N-hydroxy-3-methyl-3-(5-methylisoxazol-3-yl) methylsulfanyl-2-[(4-(4-fluorophenoxy) benzenesulfonyl)amino]butanamide, 2(S)—N-hydroxy-3-methyl-3-(5-methylisoxazol-3-yl) methylsulfanyl-2-[(4-(4-bromophenoxy) benzenesulfonyl)amino]butanamide, 2(S)—N-hydroxy-3-methyl-3-(pyrid-2-yl) methylsulfanyl-2-[(4-(4-methylphenoxy) benzenesulfonyl)amino]butanamide, 2(S)—N-hydroxy-3-methyl-3-(5-methylisoxazol-3-yl) methylsulfanyl-2-[(4-(pyrid-4-yloxy)benzenesulfonyl) amino]butanamide, 2(S)—N-hydroxy-3-methyl-3-(5-methylisoxazol-3-yl) methylsulfanyl-2-[(4-{(pyrid-4-yl) sulfanyl}benzenesulfonyl)amino]butanamide, 2(S)—N-hydroxy-3-methyl-3-(1H-imidazol-4-yl) methylsulfanyl-2-[(4-(4-bromophenoxy) benzenesulfonyl)amino]butanamide, 2(S)—N-hydroxy-3-methyl-3-(1-methyl-1H-imidazol-2-yl) methylsulfanyl-2-[(4-(4-bromophenoxy) benzenesulfonyl)amino]butanamide, 2(S)—N-hydroxy-3-methyl-3-(1-methyl-1H-imidazol-4-yl) methylsulfanyl-2-[(4-(4-bromophenoxy) benzenesulfonyl)amino]butanamide, 2(S)—N-hydroxy-3-methyl-3-(4-methyl-4H-[1,2,4]-triazol-3-yl) methylsulfanyl-2-[(4-(4-bromophenoxy) benzenesulfonyl)amino]butanamide, 2(S)—N-hydroxy-3-methyl-3-(1-methyl-4H-[1,2,4]-triazol-3-yl) methylsulfanyl-2-[(4-(4-bromophenoxy) benzenesulfonyl)amino]butanamide, and 2(S)—N-hydroxy-3-methyl-3-methylsulfanyl-2-[(4-(4-chlorophenoxy)benzenesulfonyl)amino]butanamide;

and pharmaceutically acceptable prodrugs, salts, and solvates thereof.

The present invention is further directed to methods of inhibiting metalloproteinase activity, for example in mammalian tissue, by administering a compound of the formula I, or a pharmaceutically acceptable prodrug, salt or solvate thereof. The activity of the inventive compounds as inhibitors of metalloproteinases, such as MMPs (including stromelysins, collagenases, gelatinases and/or matrilysin) and/or TNF- convertase, may be measured by any of the methods available to those skilled in the art, including in vivo and/or in vitro assays. Examples of suitable assays for activity measurements include those described in *Anal. Biochem.*, vol. 147, p. 437 (1985), *Anal. Biochem.*, vol. 180, p. 110 (1989), *FEBS*, vol. 96, p. 263 (1992) and European Patent Application No. 0 606 046.

Administration of the compounds of the formula I, or their pharmaceutically acceptable prodrugs, salts or solvates, may be performed according to any of the accepted modes of administration available to those skilled in the art. Illustrative examples of suitable modes of administration include oral, nasal, parenteral, topical, transdermal and rectal. Preferably, the mode of administration is oral.

The inventive compounds of the formula I, or their pharmaceutically acceptable prodrugs, salts or solvates, may be administered as a pharmaceutical composition in any suitable pharmaceutical form recognizable to the skilled artisan. Suitable pharmaceutical forms include, but are not limited to, solid, semisolid, liquid or lyophilized formulations, such as tablets, powders, capsules, suppositories, suspensions and aerosols. Preferably, the pharmaceutical form is a tablet or capsule for oral administration. The pharmaceutical composition may also include suitable excipients, diluents, vehicles and carriers as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling, and dissolving the ingredients as appropriate, to give the desired products for oral, parenteral, topical, intravaginal, intranasal, intrabronchial, intraocular, intraaural and/or rectal administration. Illustrative examples of such methods include those described in *Remington's Pharmaceutical Sciences*, 18th edition (1990).

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, agar, pectin, acacia, magnesium stearate and stearic acid. Illustrative liquid carriers include syrup, peanut oil, olive oil, saline solution and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of the formula I, or a pharmaceutically acceptable prodrug, salt or solvate thereof) and preferably is made up of one or more pharmaceutical dosage units. An exemplary dosage unit for a mammalian host contains an amount of from 0.1 milligram up to 500 milligrams of active compound per kilogram body weight of the host, preferably 0.1 to 200 milligrams, more preferably 50 milligrams or less, and even more preferably about 10 milligrams or less, per kilogram of the host weight. The selected dose may be administered to a mammal, for example, a human patient in need of treatment mediated by inhibition of metalloproteinase activity, by any known method of administrating the dose including: topically, for example, as an ointment or cream; orally; rectally, for example, as a suppository; parenterally by injection; or continuously by intravaginal, intranasal, intrabronchial, intraaural or intraocular infusion.

The amount of the inventive compounds, salts, solvates and/or prodrugs to be administered will vary based upon a number of factors, including the specific metalloproteinase to be inhibited, the degree of inhibition desired, the characteristics of the mammalian tissue in which inhibition is desired, the metabolic stability and activity of the particular inventive compound employed, and the mode of administration. One skilled in the art may readily determine a suitable dosage according to methods known to the art. Preferably, the amount of inventive compound of the formula I, or their pharmaceutically acceptable prodrugs, salts or solvates, administered ranges from 0.1 mg/kg body weight to 100 mg/kg body weight per day.

The inventive compounds, and the salts, solvates, and prodrugs thereof, may be prepared by employing the techniques available in the art using starting materials that are readily available. Exemplary methods of preparing the inventive compounds are described below. In the following schemes, unless otherwise indicated, R, Ar and Y are as previously defined herein.

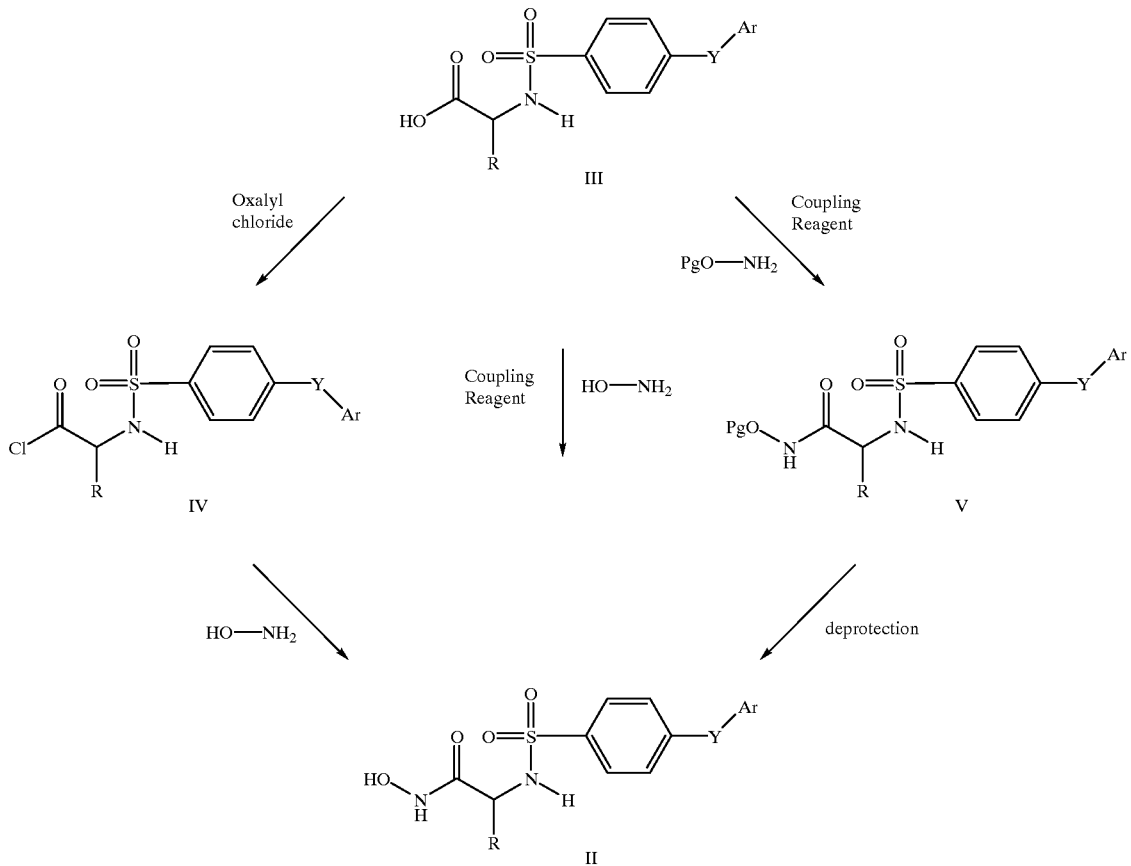

Scheme 1

As illustrated in Scheme 1, hydroxamic acids of formula II (i.e., compounds of Formula I, where X is NH—OH) can be prepared by reacting the corresponding carboxylic acids of formula III, (i.e., compounds of formula I, where X=OH) with hydroxylamine in the presence of a suitable peptide coupling reagent, for example, 1,1'-carbonyldimidazole, N-(dimethylaminopropyl)-N'-ethyl carbodiimide, benzotriazol-1-yloxy-tris(dimethylamino)phosphonium hexafluorophosphate, or propanephosphonic anhydride in an inert polar solvent, such as dimethylformamide. Alternatively, compounds of formula IV can be reacted with hydroxylamine in a suitable solvent mixture, such as THF/t-butanol/dichloromethane or water/dichloromethane, preferably at 0° C., to give hydroxamic acids of formula II. Compounds of formula IV can generally be prepared, in a form directly useful for further reaction without isolation, by allowing carboxylic acids of formula III to react with thionyl chloride or oxalyl chloride, preferably in the presence of a catalytic amount of dimethylformamide, in dichoromethane solvent at −78° C. to room temperature.

Alternatively, the coupling reactions described above may be carried out with compounds of formula III (or IV) and O-protected derivatives of hydroxylamine, where Pg is a protecting group, for example, benzyl, tert-butyl, t-butyldimethylsilyl, or t-butyldiphenylsilyl, to give compounds of formula V. Deprotection of compounds of formula V using conventional methods (for example, see "Protective Groups in Organic Synthesis", T. W. Greene and P. G. M. Wuts, Wiley-Interscience 1991) can provide compounds of formula II.

Carboxylic acids III can be prepared as shown in Scheme 2 by reaction of α-amino acids with arylsulfonyl chlorides of formula VIII, under biphasic basic conditions as described, for example, in "The Chemistry of the Amino Acids", J. P. Greenstein and M. Winitz, Robert E. Krieger Publishing Company, 1984, p. 886–889.

α-amino acid derivatives where Pg is any suitable protecting group as described, for example, in "Protective Groups in Organic Synthesis", T. W. Greene and P. G. M. Wuts, Wiley-Interscience 1991, with aryl sulfonyl chlorides VIII to give sulfonamides VI under any of a variety of reaction conditions known to those skilled in the art for the sulfonylation of amines. Deprotection of VI to give the acids III can be carried out as appropriate to the protecting group Pg. As is evident to those skilled in the art, manipulations of functionality in the amino acid side chain R or in the aryl group Ar may be readily effected at the stage of VI prior to the deprotection of VI to III. Amino acid derivatives VII, are commercially available, or are prepared according to methods familiar to those skilled in the art.

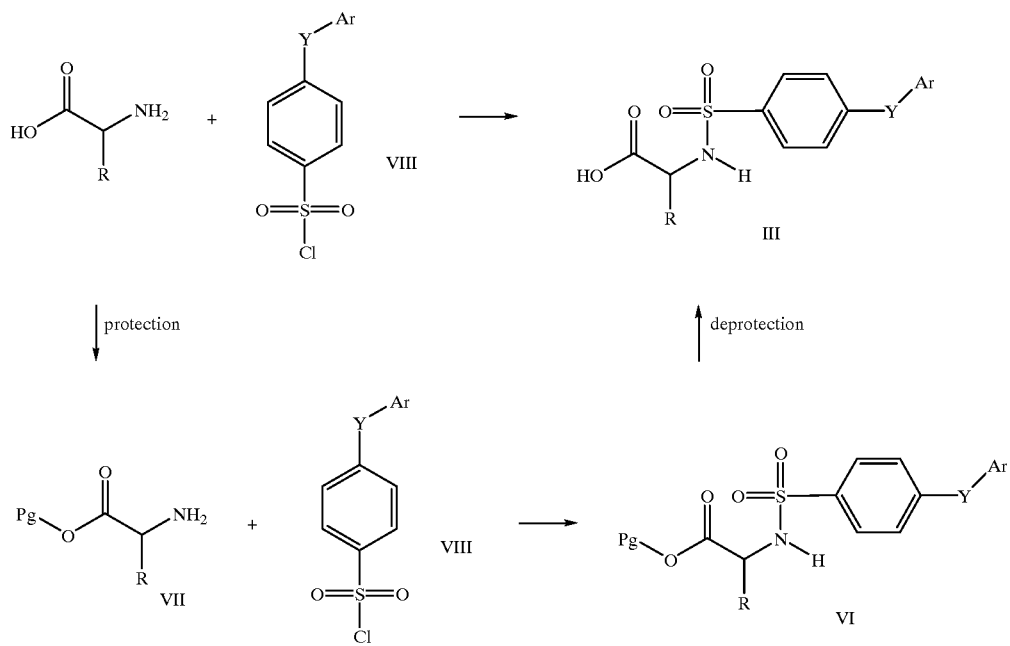

Scheme 2

α-Amino acids are commercially-available, or can be prepared according to methods familiar to those skilled in the art. Carboxylic acids III can also prepared by reaction of One variant of sequence shown in Scheme 2 that is particularly preferred in the context of the present invention is outlined in Scheme 3.

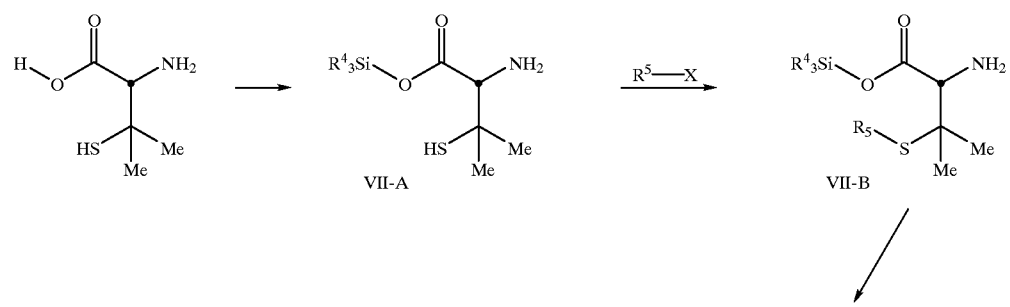

Scheme 3

-continued

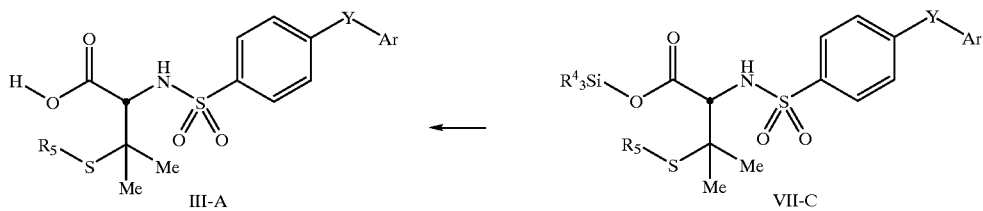

Treatment of D-penicillamine with a molar equivalent of a trialkylchlorosilane, such as trimethylsilyl chloride or dimethylthexylsilyl chloride, and a molar equivalent of a suitable base, such as 1,8-diazabicyclo[5.4.0]undec-7-ene (DBU) or diisopropylethylamine, in suitable solvent, such as DMF, at approximately 25° C. for 1 to 6 hours can provide the silyl ester VII-A. The identity of $R^4$ is dependent upon the reactant used to obtain the silyl ester VII-A, as is recognized by one skilled in the art. Without isolation, the solution of this ester VII-A can be treated with an additional DBU (at least one molar equivalent) and an alkylating reagent $R^5$-X, where $R_5$ is an alkyl group, preferably a $CH_2$-heteroaryl group, to give the S-alkylated silyl ester VII-B. Again without isolation, the resulting solution of VII-B can be treated with the aryl sulfonyl chloride Vil to provide the sulfonamide silyl ester VII-C. Upon work-up or, in the case of more stable silyl esters, brief treatment with acidic methanol, the silyl ester VII-C undergoes hydrolysis to provide the desired acid III-A.

Scheme 4

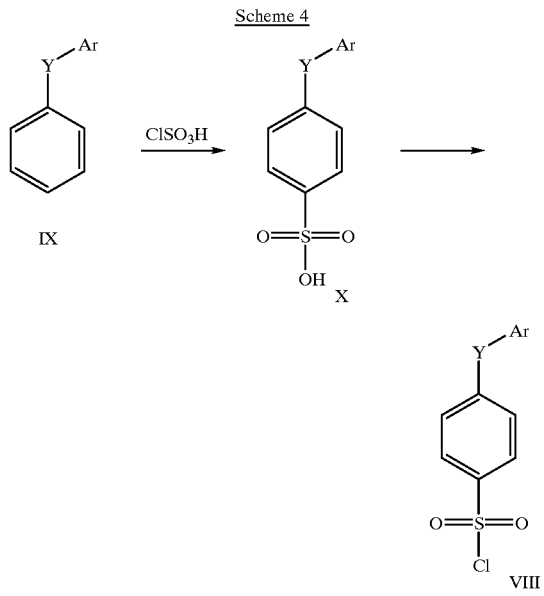

Aryl sulfonyl chlorides VIII are most readily available by chlorosulfonylation of the corresponding aryl phenyl ethers (IX, where Y═O) and aryl phenyl sulfides (IX where Y═S), as outlined in Scheme 4. In general, treatment of IX with a little over one molar equivalent of chlorosulfonic acid in a suitable inert solvent, such as 1,2-dichloroethane or dichloromethane, at –20° C. to 25° C. for a period of one to twenty-four hours can generate the corresponding sulfonic acid intermediate X. Without isolation, X is further converted to the sulfonyl chloride VIII by reaction with, for example, oxalyl chloride or thionyl chloride and cataltyic DMF. In some cases, excess chlorosulfonic acid is effective at converting IX directly to VIII via the intermediacy of X. Compounds of the formula IX are commercially-available, or may be readily prepared by those skilled in the art from commercially-available materials by the Ullman reaction.

Other compounds of the formula I may be prepared by methods known to those skilled in the art in a manner analagous to the general procedures described above. Specific examples of methods used to prepare the inventive compounds are described below along with illustrative preferred embodiments of the inventive compounds of the formula I, or their pharmaceutically acceptable prodrugs, salts or solvates.

The following specific examples are intended to be illustrative of the invention and should not be construed as limiting the scope of the invention as defined by the appended claims. These examples include preferred embodiments of the inventive compounds.

EXAMPLES

Example 1
Preparation of Intermediate Compounds of formula VIII-A.

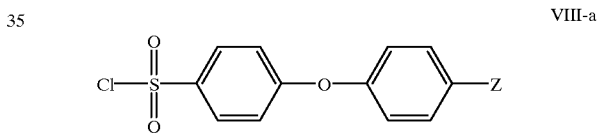

Example 1(a)
4-Phenoxybenzenesulfonyl chloride {VIII-A: Z═H}

To a stirred solution of 42.5 g (0.25 mol) of phenyl ether in 200 mL of dichloromethane at –20° C. under argon was slowly added 23.3 g (0.20 mol) of chlorosulfonic acid. After the addition was complete, the reaction was allowed to slowly warm to room temperature. After 16 hours, 150 mL of isooctane was added, and the solution was concentrated to an oily residue. Redissolution in 200 mL of 1:3 dichloromethane/isooctane and reconcentration with cooling to about 100 mL gave a solid. The supernatant was decanted, and the solid was triturated with additional isooctane and then dried in vacuo to give 55.2 g of crude 4-phenoxybenzene sulfonic acid. The crude acid was dissolved in 200 mL of dichloromethane, and 22 mL (32 g, 0.25 mol) of oxalyl chloride was added, followed by 2.5 mL of N,N-dimethylformamide. After 2 days, the reaction solution was poured into 200 mL of ice water, and extracted with 400 mL of hexane. The organic layer was washed with 100 mL of water and 100 mL of brine, dried over magnesium sulfate, and concentrated. Recrystallization of the residue from dichloromethane/isooctane gave 38.5 g of 4-phenoxybenzenesulfonyl chloride as a white solid: mp 41.5° C.; $^1$H—NMR (CDCl$_3$) δ 7.10 (apparent t, 4 H, J=7 Hz), 7.28 (t, 1H, J=7 Hz), 7.46 (t, 2H, J=8 Hz), 7.98 (d, 2H, J=8.8 Hz).

Example 1(b)
4-(4-Methylphenoxy)benzenesulfonyl chloride {VIII-A: Z=CH₃}

To a solution of 1.84 g (10.0 mmol) of 4-methyldiphenyl ether (*J. Chem. Soc., Perkin Trans.* 1; 1992, 407–408) with 2 mL of dichloromethane in an ice-bath was added a solution of chlorosulfonic acid ( 0.73 mL, 11.0 mmol) in 2 mL of dichloromethane dropwise. The resulting mixture was stirred at 0° C. to room temperature for 2 hours, and then oxalyl chloride (11.14 mL, 13.0 mmol) was added dropwise, followed by 0.15 mL of DMF. The resulting mixture was heated to 40° C. for 1 hour and then allowed to cool to room tempereature over a 2 hour period. The reaction mixture was poured into ice-pH 7 phosphate buffer (50 mL), then extracted with EtOAc:Hexane (4:3) (3×150 mL). The combined organic layers were washed with brine (75 mL). The aqueous layer was extracted with EtOAc/Hexane(4:3) (150 mL). The organic layer was dried over Na₂SO₄, then evaporated by vacuum to give crude product as white solid. This solid was triturated with hexane and collected by filtration, then dried under high vacuum to give 1.555 g (57%) of 4-(4-methylphenoxy)benzenesulfonyl chloride as white solid: mp 295–300° C.; $^1$H—NMR (DMSO-d6) δ 2.34 (s, 3H), 6.91–6.99 (dd, J=7.7,8.4 Hz, 4H), 7.24–7.27 (d, J=8.4 Hz, 2H), 7.61–7.63 (d, J=8.1 Hz, 2H).

Anal. calc. for $C_{13}H_{11}O_3SCl$: C, 55.22; H, 3.92; S, 11.34; Cl, 12.71. Found: C, 55.06; H, 3.95; S, 11.28; Cl, 12.71.

Prepared in a similar fashion were the following:

Example 1(b)
4-(4-Bromophenoxy)benzenesulfonyl chloride {VIII-A: Z=Br}: from 4-bromobiphenyl ether (supplier: Aldrich), mp 81° C.

Example 1(c)
4-(4-Chlorophenoxy)benzenesulfonyl chloride {VIII-A: Z=Cl}: from 4-chlorobiphenyl ether (supplier: Transworld), mp 61° C.

Example 1(d)
4-(4-Fluorophenoxy)benzenesulfonyl chloride {VIII-A: Z=F}: from 4-fluorobiphenyl ether (supplier: Riedel-de Haen), mp 76° C.

Example 1(e)
4-(4-Iodophenoxy)benzenesulfonyl chloride {VIII-A: Z=I} from 4-iodobiphenyl ether (supplier: Transworld): mp 85–88° C.

Example 1(f)
4-(4-Cyanophenoxy)benzenesulfonyl chloride {VIII-A: Z=CN}: from 4-cyanobiphenyl ether (supplier: Transworld): mp 98–102° C.

Example 1(g)
4-(4-Trifluoromethyphenoxy)benzenesulfonyl chloride {VIII-A: Z=CF₃}: from 4-trifluoromethylbiphenyl ether (*J. Chem. Soc. Perkin Trans.*1 1988, 3229–3232): mp 265–270° C.; $^1$H—NMR (CDCl₃) δ 7.04 (d, J=8.4 Hz, 2H), 7.14 (d, J=8.7 Hz, 2H), 7.65 (d, J=8.8 Hz, 2H), 7.73 (d, J=8.7 Hz, 2H).

Anal. calc. for $C_{13}H_8O_3SF_3Cl$ (336.71): C, 46.34; H, 2.39; S, 9.52. Found: C, 46.34; H, 2.49; S, 9.37.

Example 1(h)
4-(Pyrid-2-yl)oxybenzenesulfonyl chloride

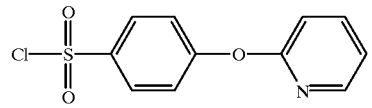

From 2-phenoxypyridine (supplier: ICN): $^1$H NMR (CDCl₃) d 8.25 (m, 1H), 8.05 (d, 2H, J=9 Hz), 7.81 (t, 1H, J=8 Hz), 7.34 (d, 2H, J=9 Hz), 7.15 (dd, 1 H, J=7 & 5 Hz), 7.06 (d, 1H, J=8 Hz).

Example 2
Preparation of Intermediates of Formula VIII.

Example 2(a)
4-(Pyrid-4-yl)oxybenzenesulfonyl chloride hydrochloride

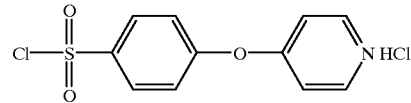

To a suspension of 4-(pyrid-4-yl)oxybenzenesulfonic acid (1.3 kg) in acetonitrile (8 L), was added N,N-dimethylformamide (12.35 mL), and the viscous reaction mixture was heated to 75° C. Thionyl chloride (756 mL) was added to the reaction mixture over 30 minutes. The reaction mixture slowly became less viscous and became homogeneous after 45 minutes, which indicated the reaction was complete. A portion of the solvent (4 L) was evaporated under vacuum and tert-butyl methyl ether (4 L) was added. The resulting slurry was filtered under inert atmosphere. The filter cake was rinsed with tert-butyl methyl ether (2 L) and the solid dried under vacuum to yield 4 -(pyrid-4-yl)oxybenzenesulfonyl chloride hydrochloride (1.35 kg) as a hygroscopic, off-white solid of pearlescent flakes: mp 182° C.; $^1$H NMR (CDCl₃): δ 8.87 (d, J=7 Hz, 2H), 8.24 (d, J=8.5 Hz, 2H), 7.50 (d, J=8.5 Hz, 2H), 7.43 (d, J=7 Hz, 2H).

The starting material was prepared as follows:

To a vigorously stirred solution of 1.00 kg (5.85 mol) of 4-phenoxypyridine (*Tetrahedron*, 1978, 34, 2069–2076) in dry 1,2-dichloroethane (3000 L) at −10° C. under a stream of argon was added chlorosulfonic acid (974 mL) at a rate so as to maintain the reaction temperature below 0° C. After half of the chlorosulfonic acid was added, the exotherm stopped. The cooling bath was removed and the addition of chlorosulfonic acid continued over 3 hours while the reaction solution warmed to room temperature. While continually purging with argon, the vigorously stirred reaction mixture was heated to 45° C. After 20 hours, the reaction mixture was cooled to room temperature and slowly poured into vigorously stirred ice cold water (5 L). Potassium phosphate tribasic (212 g) was added as a solid to the mixture and this was stirred for 10 minutes followed by addition of sodium hydroxide (2M) to pH 2. After stirring for 1 hour, the pH was changed to 7 by the addition of sodium hydroxide (2M). Agitation was continued for 5 minutes; then the organic layer was drained off and discarded. The mixture was extracted a second time with dichloromethane (2 L), and the organic layer drained off and discarded. The remaining aqueous phase was extracted with tetrabutylammonium bromide (940 g) in dichloromethane (6L), adjusting the aqueous phase to pH 7 with 2M aq. sodium hydroxide as necessary. The extraction was repeated two more times and the combined organic layers were dried over magnesium sulfate, filtered, and concentrated. The residue was dissolved with 20% ethanol in ethyl acetate (8 L, dry), and hydrogen chloride gas added to achieve a pH of 1. The solid was filtered off, and the filter cake was rinsed with the precipitation solvent mixture (20% ethyanol in ethyl acetate, 2 L). The solid was dried under vacuum at 45° C. for 15 hours to yield 4-(pyrid-4-yl)oxybenzenesulfonic acid (1.3 kg) as a white powdery solid.

mp dec. >275° C.; $^1$H NMR (DMSO-d$_6$): δ 8.86 (dd, J=1.5, 7.4 Hz, 2H), 7.84 (dd, J=1.5, 7 Hz, 2H), 7.54 (dd, J=1.5, 7.4 Hz, 2H), 7.35 (dd, J=1.5, 7 Hz, 2H).

Anal. calc. for C$_{11}$H$_9$NO$_4$S: C, 52.58; H, 3.61; N, 5.57; S, 12.76. Found: C, 52.50; H, 3.69; N, 5.51; S, 12.67.

Example 2(b)
4-(Pyrid-4-yl)sulfanylbenzenesulfonyl chloride hydrochloride

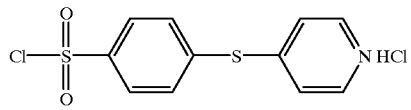

Prepared as in Example 2(a) from 4-(phenylsulfanyl) pyridine (prepared as in *J. Am. Chem. Soc.* 1937, 59, 2697): mp 194° C.

$^1$H NMR (CDCl3) δ 8.61 (d, J=7 Hz, 2H), 8.25–8.20 (m, 2H), 7.93–7.8(m, 2H), 7.48 (d, J=7 Hz).

Example 3
Preparation of Compounds of Formula III-A

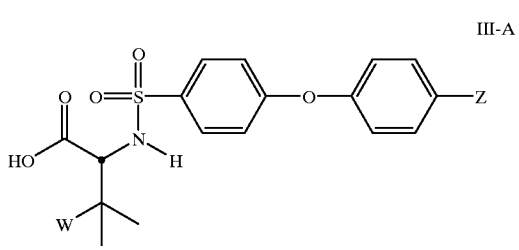

Example 3(a)
S—[(1-Benzyl-1H-imidazol-2-yl)methyl]—N—[4-(4-fluorophenoxy) benzenesulfonyl]-D-penicillamine {III-A, W=(1-Benzyl-1H-imidazol-2-yl)CH$_2$S, Z=F}

To a suspension of D-penicillamine (0.500 g, 3.35 mmol) in DMF (7 mL) was added diisopropylethylamine (0.70 mL., 4.0 mmol), followed by dimethylthexylsilyl chloride (0.725 mL, 3.68 mmol). After 2.5 hours at room temperature, the solution was cooled to 0° C., and DBU (1.59 mL, 10.7 mmol) was added, followed by 2-chloromethyl-1-benzyl-1H-imidazole hydrochloride (0.977 g., 4.02 mmol, Maybridge). The solution was allowed to warm to room temperature. After 3 hours, the solution was recooled to 0° C., diisopropylethylamine (0.70 mL., 4.0 mmol) was added, followed by 4-(4-fluorophenoxy) benzenesulfonyl chloride (1.01 g., 4.00 mmol). The solution was allowed to slowly warm to room temperature, stirred for 5 h, and then partitioned between brine and ethyl acetate. The organic layer was washed with brine, filtered through celite, and concentrated. The residue was dissolved in methanol (50 mL), and treated with acetic acid (0.400 mL). After 2 hours at room temperature, the solution was concentrated, and the residue was purified on silica, eluting with 5% methanol/dichloromethane.

Trituration of the residue with 25% diethyl ether/hexane gave S—[(1-benzyl-1H-imidazol-2-yl)methyl]—N—[4-(4-fluorophenoxy)benzenesulfonyl]-D-penicillamine as a white solid in 52% yield: mp 172–173° C.; $^1$H—NMR (CDCl$_3$) δ 1.29 (s, 3H), 1.44 (s, 3H), 3.75–4.02 (m, 3H), 5.29 (s, 2H), 6.95–7.65 (m, 15H).

Anal calcd. for C$_{28}$H$_{28}$FN$_3$O$_5$S$_2$: C, 59.03; H, 4.95; N, 7.38; S, 11.26. Found: C, 58.77; H, 4.97; N, 7.33; S, 11.07.

Prepared in a similar manner were Examples 3(b) to 3(n):

Example 3(b)
N-[4-(4-Bromophenoxy)benzenesulfonyl]—S—[(1-benzyl-1H-imidazol-2-yl)methyl]-D-penicillamine {III-A, W=(1-Benzyl-1H-imidazol-2-yl)CH$_2$S, Z=Br}.

mp 176–177° C.; H—NMR (CD$_3$OD) δ 1.36 & 1.41 (2s, 6H), 3.67 (s, 1H), 4.00 (m, 2H), 5.36 (s, 2H), 7.01–7.85 (m, 15H); FAB HRMS: expected (M+Cs)=761.9708. Found (M+Cs)=761.9728

Anal calcd. for C$_{28}$H$_{28}$BrN$_3$O$_5$S$_2$: C, 53.33; H, 4.48; N, 6.66; S, 10.17. Found: C, 53.25; H, 4.43; N, 6.59; S, 10.06.

Example 3(c)
N-[4-(4-Fluorophenoxy)benzenesulfonyl]—S—[(pyrid-2-yl)methyl]-D-penicillamine {III-A, W=(pyrid-2-yl)CH$_2$S, Z=F} mp 194° C.; $^1$H—NMR (DMSO-d6) δ 1.33 (s, 6H), 3.85–3.97 (m, 3H), 7.12 (d, J=9 Hz, 2H), 7.18–7.54 (m, 6H), 7.70–7.79 ( m, 1H), 7.84 (d, J=9 Hz, 2H), 8.3 (d, J=10 Hz, 1H), 8.4 (d, J=4 Hz, 1H), 12.68 (br s, 1H).

Anal. calc. for C$_{23}$H$_{23}$FN$_2$O$_5$S$_2$: C, 56.31; H, 4.73; N, 5.71. Found: C, 56.06; H, 4.78; N, 5.64.

Example 3(d)
N-[4-(4-Bromophenoxy)benzenesulfonyl]—S—[(pyrid-2-yl)methyl]-D-penicillamine {III-A, W=(pyrid-2-yl)CH$_2$S, Z=Br} mp 165–168° C.; $^1$H—NMR (CD$_3$OD) δ 1.39 (s, 3H), 1.45 (s,3), 3.92–3.99 (m, 2H), 7.03–7.12 (dd, J=9 & 2 Hz, 4H), 7.24–7.26 (m, 1H), 7.53–7.60 (m, 3H), 7.82–7.90 (m, 3H), 8.52 (d, J=3 Hz, 1H).

Anal. calc. for C$_{23}$H$_{24}$N$_3$O$_5$S$_2$F•0.2 H$_2$O: C, 49.77; H, 4.25; N, 5.05. Found: C, 49.93; H, 4.19; N, 4.12.

Example 3(e)
N-[4-(4-Fluorophenoxy)benzenesulfonyl]—S—[(pyrid-3-yl)methyl]-D-penicillamine {III-A, W=(pyrid-3-yl)CH$_2$S, Z=F}.

mp 200–201° C.; $^1$H—NMR (DMSO-d6) δ 1.35 (s, 6H), 3.87 (m,3H), 7.11–8.60 (m, 12H), 8.25 (br s, 1H).

Anal. calc. for C$_{23}$H$_{23}$FN$_2$O$_5$S$_2$•0.3 H$_2$O: C, 55.49; H, 4.82; N, 5.63. Found: C,55.34; H, 4.67; N, 5.6.

Example 3(f)
N-[4-(4-Fluorophenoxy)benzenesulfonyl]—S—[(pyrid-4-yl)methyl]-D-penicillamine {III-A, W=(pyrid4-yl)CH$_2$S, Z=F}.

mp 197° C.; $^1$H—NMR (DMSO-d6) δ 1.34 (s, 6H), 3.80–4.00 (m, 3H), 7.00–8.80 (m, 13H). 8.25 (s, 1H).

Anal. calc. for C$_{23}$H$_{23}$FN$_2$O$_5$S$_2$•0.1H$_2$O: C, 56.11; H, 4.75; N, 5.69. Found: C, 55.78; H, 4.75; N, 5.73.

Example 3(g)
N-[4-(4-Methylphenoxy)benzenesulfonyl]—S—[(pyrid-2-yl)methyl]-D-penicillamine {III-A, W=(pyrid-2-yl)CH$_2$S, Z=Me} mp 185–187° C.; $^1$H—NMR (CD$_3$OD) δ 1.39 (s, 3H) 1.44 (s, 3H), 2.39 (s, 3H), 3.92–4.01 (m, 3H), 6.98–7.04 (m, 4H), 7.25–7.28 (m, 3H), 7.54 (d, J=7 Hz, 2H), 7.82–7.85 (m, 3H), 8.42 (d, J=6 Hz, 1H).
Anal. calc. for $C_{24}H_{26}N_2O_5S_2 \cdot 0.35\ CH_2Cl_2$: C, 56.64; H, 5.21; N, 5.43. Found: C, 56.48; H, 5.32; N, 5.67.

Example 3(h)
N-[4-(4-Cyanophenoxy)benzenesulfonyl]—S—[(pyrid-2-yl)methyl]-D-penicillamine {III-A, W=(pyrid-2-yl)$CH_2$S, Z=CN}
mp 170–173° C.; $^1$H—NMR (CD$_3$OD) δ 1.42 (s, 3H), 1.44 (s, 3H), 3.82–4.01 (m, 3H), 7.19–7.23 (m, 5H), 7.60 (d, J=5 Hz, 1H), 7.79 (d, J=4 Hz, 3H), 7.95–7.98 (d, J=9 Hz, 2H) 8.42–8.43 (d, J=5 Hz,1H).
Anal. calc. for $C_{24}H_{23}N_3O_5S_2 \cdot 0.7H_2O \cdot 0.6CH_2Cl_2$: C, 52.23; H, 4.82; N, 7.28 Found: C, 52.22; H, 4.87; N, 7.38.

Example 3(i)
N-[4-(4-Iodophenoxy)benzenesulfonyl]—S—[(pyrid-2-yl)methyl]-D-penicillamine {III-A, W=(pyrid-2-yl)$CH_2$S, Z=I}
mp 177–180° C.; $^1$H—NMR (CD$_3$OD) δ 1.40 (s, 3H), 1.44 (s, 3H), 3.87–4.01 (m, 3H), 6.91 (d, J=8 Hz, 2H), 7.10 (d, J=9 Hz, J=2H), 7.32–7.56 (m, 1H), 7.77 (d, J=8 Hz, 1H), 7.81–7.89 (m, 4H), 8.44 (d, J=5 Hz, 2H).
Anal. calc. for $C_{23}H_{23}N_2O_5S_2I \cdot 0.1H_2O$: C, 46.15; H, 3.94; N, 4.65. Found: C, 46.15; H, 3.95; N, 4.51.

Example 3(j)
N-[4-(4-(trifluoromethyl)phenoxy)benzenesulfonyl]—S—[(pyrid-2-yl)methyl]-D-penicillamine {III-A, W=(pyrid-2-yl)$CH_2$S, Z=CF$_3$}
mp 182–185° C.; $^1$H—NMR (CD$_3$OD) δ 1.36 (s, 3H),1.41 (s, 3H), 3.83–3.98 (m, 3H), 7.14–7.30 (m, 4H), 7.51 (d, J=8 Hz, 2H), 7.69–7.91 (m, 4H), 8.41 (d, J=4 Hz, 2H).
Anal. calc. for $C_{24}H_{23}N_2O_5S_2F_3 \cdot 0.35$ hexane: C, 54.92; H, 4.93; N, 4.91. Found: C, 55.07; H, 5.01; N, 5.06.

Example 3(k)
N-[4-(4-Bromophenoxy)benzenesulfonyl]—S—[(5-methylisoxazol-3-yl)-methyl]-D-penicillamine {III-A, W=(5-methylisoxazol-3-yl)$CH_2$S, Z=Br}
mp 119° C.; $^1$H—NMR (DMSO-d6) δ 1.35 (s, 6H), 2.4 (s, 3H), 3.3 (br s,1H), 3.73 (d, J=14 Hz, 1H), 3.79 (d, J=14 Hz, 1H), 6.21 (s, 1H), 7.1–7.2 (br s, 1H), 7.13 (d, J=9 Hz, 2H), 7.15 (d, J=9 Hz, 2H), 7.68 (d, J=9 Hz, 2 H), 7.82 (d, J=9 Hz, 2H).
Anal. calc. for $C_{22}H_{23}BrN_2O_6S_2 \cdot 0.1\ H_2O \cdot 0.3\ CHCl_3$: C, 45.16; H, 3.99; N, 4.72. Found: C, 45.24; H, 4.03; N, 4.7.

Example 3(l)
N-[4-(4-Fluorophenoxy)benzenesulfonyl]—S—[(5-methylisoxazol-3-yl)methyl]-D-penicillamine {III-A, W=(5-methylisoxazol-3-yl)$CH_2$S, Z=F}
mp 112–113° C.; $^1$H—NMR (DMSO-d6) δ 1.35 (s,6H),2.40 (s, 3H), 3.3–3.97 (br s,1H), 3.73 (d, J=13 Hz, 1H), 3.79 (d, J=13 Hz, 1H), 6.24 (s, 1H), 6.9–7.2 (br s, 1H), 7.07 (d, J=9 Hz, 2H), 7.2–7.38 (m, 4H), 7.8 (d, J=9 Hz, 2H).
Anal. calc. for $C_{22}H_{23}FN_2O_6S_2 \cdot 0.1H_2O \cdot 0.3\ CHCl_3$: C, 50.33; H, 4.45; N, 5.26. Found: C, 50.27; H, 4.35; N, 5.3.

Example 3(m)
S-Benzyl—N—[4-phenoxybenzenesulfonyl]-D-penicillamine {III-A, W=PhCH$_2$S, Z=H}
mp 92–95° C.; $^1$H—NMR (CDCl$_3$) δ 1.36 (s, 3H), 1.59 (s, 3H), 2.25 (br s, 1H), 5.46 (d, J=10 Hz, 2H), 6.99–7.39 (m, 7H), 7.61–7.85 (m, 7H).
Anal. calc. for $C_{24}H_{26}NO_5S_2 \cdot 0.8\ NH_3$: C, 59.32; H, 5.89; N, 5.13. Found: C, 59.58; H, 5.92; N, 5.13.

Example 3(n)
S—(t-Butoxycarbonyl)methyl—N—[4-(4-fluorophenoxy)benzenesulfonyl]-D-penicillamine {III-A, W=t-BuO$_2$CCH$_2$S, Z=F}
mp 75° C.; $^1$H—NMR (CDCl$_3$) δ 1.26 (s, 3H), 1.34 (s, 3H), 1.43 (s, 9H), 3.16 (d, J=15 Hz, 1H), 3.26 (d, J=15 Hz, 1H), 3.76 (d, J=8 Hz, 1H), 6.5 (br s, 1H), 6.94 (d, J=9 Hz, 2H), 6.97–7.1 (m, 4H), 7.82 (d, J=9 Hz, 2H).
Anal. calc. for $C_{23}H_{28}FNO_7S_2 \cdot 0.2CHCl_3$: C, 51.84; H, 5.29; N, 2.61. Found; C, 51.79; H, 5.26; N, 2.70.

Example 3(o)
N-[4-(4-Bromophenoxy)benzenesulfonyl]—S—[1-methyl-1H-imidazol-2-yl)methyl]-D-penicillamine {III-A, W=(1-methyl-1H-imidazol-2-yl)$CH_2$S, Z=Br}:
$^1$H NMR (DMSO): δ 1.20 (s, 3H), 1.27 (s, 3H), 3.61 (s, 3H), 3.79 (s, 1H), 3.93 (s, 2H), 6.81 (s, 1H), 7.06–7.14(m, 5H), 7.62 (d, 2H, J=9.0 Hz), 7.70 (d, 2H, J=9.0 Hz); ESIMS Calcd for $C_{22}H_{24}O_5N_3S_2Br$: 554/556. Found: 554/556.
Anal. Calcd for $C_{22}H_{24}O_5N_3S_2 \cdot 0.08$ HOAc: C, 45.59; H, 4.38; N, 7.51; S, 11.47; Br, 14.29.
Found: C, 45.55; H, 4.37; N, 7.37; S, 11.46, Br, 14.34

Example 3(p)
N-[4-(4-Chlorophenoxy)benzenesulfonyl]-D-tert-leucine {III-A, W=CH$_3$, Z=Cl}.
To a suspension of D-tert-leucine (0.250 g., 1.91 mmol, Aldrich) in dichloromethane (3 mL) and DMF (1.5 mL) was added N-methylmorpholine (0.50 mL., 4.55 mmol), followed by chlorotrimethylsilane (0.30 mL., 2.36 mmol) and the mixture stirred at room temperature for 6 hours. Diisopropylethylamine (0.300 mL., 1.72 mmol) was added, followed by 4-(4-chlorophenoxy)benzenesulfonyl chloride (0.636 g., 2.10 mmol, from example 1(c)) portionwise via a solid addition funnel. The resulting solution was then stirred at room temperature for 3.5 hours, and then partitioned between ethyl acetate and 1N aq. sodium bisulfate. The organic layer was washed with brine, dried over MgSO4, and concentrated. The residue was purified on silica gel, eluting with 40% ethyl acetate in hexane followed by 10% methanol in dichloromethane, to give N-[4-(4-chlorophenoxy)benzenesulfonyl]-D-tert-leucine as a white solid in 62% yield: mp 138–140° C.; $^1$H—NMR (CDCl$_3$) δ 0.949 (s, 9H), 3.51–3.54 (d, 1H, J10.3 Hz), 5.55–5.59 (m, 1H), 6.94–7.83 (m, 8H).
FAB HRMS: expected (M+H)=398.0829, found (M+H)=398.0840

Examples 3(q), 3(r), and 3(s) were prepared following the procedure provided in Example 3(p):

Example 3(q)
N-[4-(4-Fluorophenoxy)benzenesulfonyl]-D-tert-leucine {III-A, W=CH$_3$, Z=F}.
mp 170–174° C.

Example 3(r)
N-[4-Phenoxybenzenesulfonyl]-D-tert-leucine {III-A, W=CH$_3$, Z=H}
mp 147–150° C.; $^1$H—NMR (CDCl$_3$) δ 0.98 (s, 9H), 3.59 (d, J=10.7 Hz, 1H), 5.17 (d, J=10.5 Hz, 1H), 6.99–7.43 (m, 6H), 7.77 (d, J=7.0 Hz, 3H).
Anal. calc. for $C_{18}H_{21}NO_5S \cdot 0.3\ H_2O$ (368.82): C, 58.61; H, 5.90; N, 3.80.
Found: C, 58.72; H, 5.90; N, 3.74.

Example 3(s)

N-[4-(4-Bromophenoxy)benzenesulfonyl]-D—(β-hydroxy) valine {III-A, W=OH, Z=Br}

Starting from D-3-hydroxyvaline, which was prepared by the method described in *J. Org. Chem.* 1996, 61, 2582–2583; mp 153–4° C. $^1$H NMR (DMSO-d6): ∂ 0.88 (s, 3H), 1.07 (s, 3H), 2.80 (d, 1H, J=6.0 Hz), 6.79 (d, 1H, J=6.0 Hz), 7.06–7.11 (m, 4H), 7.62 (d, 2H, J=9.0 Hz), 7.76 (d, 2H, J=8.1 Hz); ESIMS Calcd for $C_{17}H_{18}O_6NSBr$: 444/446.

Found: 444/446.

Anal. Calcd for $C_{17}H_{18}BrNO_6S$: C, 45.96; H, 4.08; N, 3.15; S, 7.22; Br, 17.98. Found: C, 45.73; H, 4.05; N, 3.08; S, 7.08, Br, 17.91.

In a similar fashion may be prepared:

Example 3(t)

N-[4-(4-Bromophenoxy)benzenesulfonyl]-D-tert-leucine {III-A, W=CH$_3$, Z=Br}

Example 3(u)

N-[4-(4-Chlorophenoxy)benzenesulfonyl]-D—(β-hydroxy) valine {III-A, W=OH, Z=Cl}

Example 3(v)

N-[4-(4-Chlorophenoxy)benzenesulfonyl]-D-valine {III-A, W=H, Z=Cl}

Example 4

Preparation of Compounds of Formula III.

Prepared in a similar manner as in Example 3(a) were Examples 4(a), 4(b) and 4(c).

Example 4(a)

S-Benzyl—N—[4-(pyrid-4-yl)oxybenzenesulfonyl]-D-penicillamine

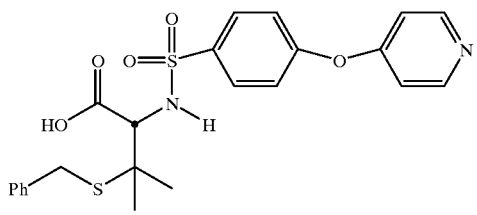

mp 105–110° C.; $^1$H—NMR (DMSO-d6) δ 1.35 (s, 6H), 3.39–3.85 (m, 2H), 7.07 (d, J=6 Hz, 2H), 7.34–7.39 (m, 4H), 7.95 (d, J=8 Hz, 3H), 8.41 (d, J=9 Hz, 2H), 8.58 (d, J=6 Hz, 2H).

Anal. calc. for $C_{23}H_{24}N_2O_5S_2$: C, 58.45; H, 5.12; N, 5.93. Found: C, 58.36; H, 5.16; N, 5.89

Example 4(b)

S—[(5-Methylisoxazol-3-yl)methyl]—N—[4(pyrid-4-yl)oxybenzenesulfonyl]-D-penicillamine.

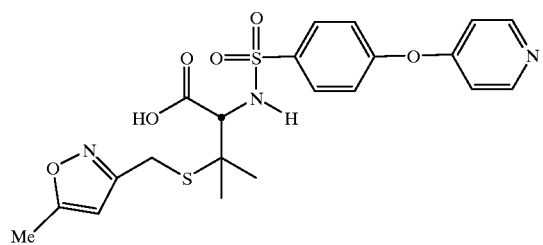

mp 90–92° C. $^1$H NMR (CDCl$_3$): δ 1.42 (s, 3H), 1.46 (s, 3H), 2.40 (s, 3H), 3.80 (dd, 3H, J=14.3, 19.3 Hz), 5.75 (d, 1H, J=10.2 Hz), 6.02 (s, 1H), 6.82 (d, 2H, J=6.5 Hz), 7.08 (d, 2H, J=8.7 Hz), 7.98 (d, 2H, J=8.7 Hz), 8.40 (d, 2H, J=6.5 Hz); FAB HRMS Calcd for $C_{21}H_{24}O_6N_3S_2$: 478.1107. Found: 478.1117.

Anal. Calcd for $C_{21}H_{23}O_6N_3S_2 \cdot 1.5 H_2O$: C, 49.99; H, 5.19; N, 8.33; S, 12.71. Found: C, 49.57; H, 4.94; N, 8.15; S, 12.43.

Example 4(c)

S—[(5-Methylisoxazol-3-yl)methyl]—N—[4(pyrid-4-yl) sulfanylbenzenesulfonyl]-D-penicillamine.

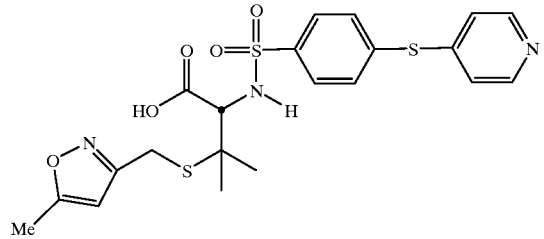

mp 79–85° C. $^1$H NMR (DMSO-d$_6$) δ 1.27 (s, 3H), 1.29 (s, 3H), 2.33 (s, 2H), 3.73 (dd, 2H, J=1.6, 12.6 Hz), 3.77–3.83 (m, 1H), 6.14 (d, 1H, J=1.6 Hz), 7.13 (dd, 1H, J=1.6, 4.7 Hz), 7.68 (d, 2H, J=8.7 Hz), 7.85 (d, 2H, J=8.7 Hz), 8.32–8.47 (m, 3H). IR (KBr): 3425, 3248, 1713, 1608, 1557, 1478, 1337, 1161, 1096, 1077, 756, 620 cm$^{-1}$. HR FABMS Calcd for $C_{21}H_{24}N_3O_5S_3$ (M+H): 494.0878. Found: 494.0890.

Anal. Calcd for $C_{21}H_{23}N_3O_5S_3 \cdot 0.1\ C_7H_{16} \cdot 0.3\ CHCl_3$: C, 48.98; H, 4.65; N, 7.79; S, 17.83. Found: C, 48.77; H, 4.69; N, 7.63; S, 17.76.

Prepared in a manner similar to Example 3(p) was Example 4(d).

Example 4(d)

N-[4-(Pyrid-2-yl)oxy)benzenesulfonyl]-D-tert-leucine.

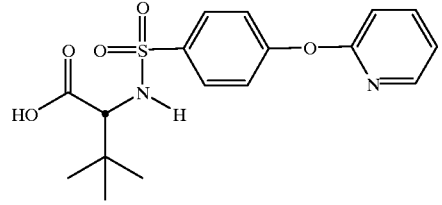

mp 202° C. (decomp); $^1$H—NMR (CDCl$_3$) δ 1.02 (s, 9H), 3.55 (d, 1H, J=10 Hz), 5.30 (d, 1H, J=10 Hz), 7.05–8.21 (m, 8H); FAB HRMS: Expected ( M+Cs)$^+$=497.0147. Found (M+Cs)$^+$=497.0160.

Example 4(e)

N-[4-(4-(Furan-3-yl)phenoxy)benzenesulfonyl]—S—[(pyrid-2-yl)methyl]-D-penicillamine.

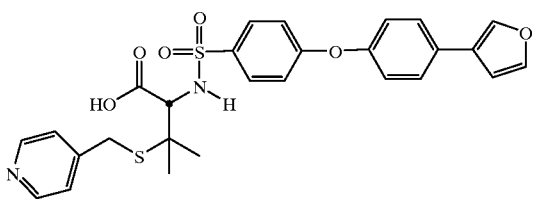

To a suspension of 221 mg (0.40 mmol) of N-[4-(4-bromophenoxy) benzenesulfonyl]—S—[(pyrid-2-yl)methyl]-D-penicillamine (from example 3(d)) in 2 mL of benzene and 2 mL of 2M aqueous $Na_2CO_3$ solution was added a solution of 71 mg (0.48 mmol) of 3-furan boronic acid (J. Org. Chem. 1984, 49, 5237–5243) in 2 mL of EtOH. To the resulting mixture was added solid $Pd(PPh_3)_4$ (46 mg, 0.04 mmol) under a flow of Ar. The mixture was heated at 80° C. with vigorous stirring for 72 hours, cooled to room temperature, and partitioned between ehtyl acetate and $AcOH/H_2O$ buffer (pH 3). The aqueous layer was adjusted to pH of 3 by adding AcOH, then extracted with EtOAc (2×70 mL). The combined organic layers were washed with brine, dried over $Na_2SO_4$, and concentrated. The residual yellow solid was chromatographed on silica gel, eluting first with $CH_2Cl_2$, then with 10% methanol in dichloromethane to elute the product fractions. After concentration of the product-containing fractions, the residue was triturated with hexane/t-butyl methyl ether, and the solid was collected by filtration. The solid was dried in high vacuum to give 166.1 mg (77%) of N-[4-(4-(furan-3-yl)phenoxy)benzenesulfonyl]—S—[(pyrid-2-yl)methyl]-D-penicillamine as a yellow solid: mp 185–189° C.; $^1$H—NMR ($CDCl_3$) δ 1.40 (s, 3H) 1.44 (s, 3H), 3.32–4.01 (m, 3H), 6.83 (s, 1H), 7.10–7.13 (m, 4H), 7.22–7.23 (m, 2H), 7.57–7.92 (m, 8H), 8.42 (d, J=4 Hz, 2H).
Anal. calc. for $C_{27}H_{26}N_2O_6S_2$: C, 60.20; H, 4.87; N, 5.20. Found: C, 60.00; H, 4.88; N, 4.94.

Example 5
S-Carboxymethyl—N—[4-(4-fluorophenoxy)benzenesulfonyl]-D-penicillamine

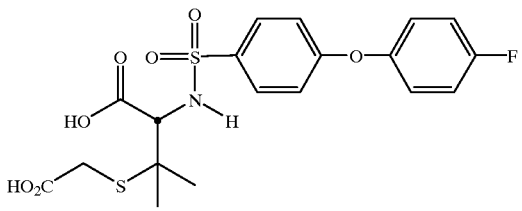

To a solution of S—(t-Butoxycarbonyl)methyl—N—[4-(4-fluorophenoxy)benzenesulfonyl]-D-penicillamine (188.8 mg, 0.367 mmol) in 3.4 mL of dichloromethane at 20° C. was added trifluoroacetic acid (0.85 mL). The solution was stirred for 16 h and concentrated in vacuo. The residue was partitioned between ethyl acetate (25 mL) and 1 M aq. phosphate buffer (pH 7). The aqueous layer was extracted with two additional portions of ethyl acetate (25 mL), and the combined organic layers were washed with brine, dried over sodium sulfate, and concentrated. The residue was triturated with diethyl ether (5 mL) to give 67 mg (40%) of S-Carboxymethyl—N—[4-(4-fluorophenoxy)benzenesulfonyl]-D-penicillamine as an off-white solid: mp 69° C.; $^1$H—NMR (DMSO-d6) δ 1.32 (br s, 6H), 3.25–3.5 (br m, 3H), 7.12 (d, J=8 Hz, 2H), 7.2–7.5 (m, 4H), 7.82 (d, J=8 Hz, 2H), 8.00–8.40 (br s, 1H), 12.5–13.2 (v br s, 1H).

Anal. calc. for $C_{19}H_{20}FNO_7S_2$•0.7 $H_2O$•0.2 $Et_2O$: C, 49.04; H, 4.86; N, 2.89. Found: C, 49.04; H, 4.91; N, 2.78.

Example 6
Preparation of Compounds of Formula III.

Example 6(a)
S-Methyl—N—[4-(phenoxy)benzenesulfonyl]-D-penicillamine {III-A, W=$CH_3$S, Z=H}

To a solution of S-methyl—N—[4-(phenoxy)benzenesulfonyl]-D-penicillamine methyl ester (0.250 g., 0.610 mmol) in DMSO (3 mL) at room temperature was added sodium thiomethoxide (171 mg., 2.44 mmol) in one portion. The solution was heated at 45° C. for18 hours, and then cooled to 0° C. and acidified to pH=5 using 1N aqueous sodium bisulfate. The mixture was partitioned between ethyl acetate and water, and the organic phase was washed with brine, dried over $MgSO_4$, and concentrated. The residue was purified on silica eluting with 8 to 12% methanol in dichloromethane to give S-methyl—N—[4-(phenoxy)benzenesulfonyl]-D-penicillamine as a white solid in 95% yield: mp 156–158° C.; $^1$H—NMR (DMSO-d6) δ 1.28 (s, 3H), 1.31 (s, 3H), 1.97 (s,3H), 7.08–7.82 (m, 10H).
Anal. calc. for $C_{18}H_{21}NO_5S_2$•0.5 $CH_2Cl_2$: C, 50.73; H, 5.06; N, 3.20. Found: C, 50.46; H, 5.00; N, 3.24.
The starting material was prepared as follows:
(i) S-Methyl-D-penicillamine methyl ester To a 0° C. solution of D-penicillamine methyl ester hydrochloride (0.250 g., 1.25 mmoles) in DMF (4 mL) was added DBU (0.382 ml., 2.56 mmoles), followed by methyl iodide (0.081 ml., 1.31 mmoles). After 1 hour, the solution was partitioned between brine and ethyl acetate, and the organic layer was dried over sodium sulfate and concentrated. The residue was purified on silica, eluting with 6% methanol in dichloromethane to give S-methyl-D-penicillamine methyl ester as a colorless oil in 81% yield: $^1$H—NMR (CDCl3) δ 1.25 (s, 3H) 1.35 (s, 3H), 2.02 (s, 3H), 3.44 (s,1H), 3.72 (s, 3H); FAB HRMS:expected (M+H)=178.0902, found (M+H)=178.0905.
(ii) S-Methyl—N—[4-(phenoxy)benzenesulfonyl]-D-penicillamine methyl ester To a solution of S-methyl-D-penicillamine methyl ester (0.160 g., 0.904 mmol) and diisopropylethylamine (0.172 mL, 0.99 mmol) in dichloromethane (3 mL) was added 4-phenoxybenzenesulfonyl chloride (0.304 g, 1.13 mmol) via solid addition funnel. After 2.5 hours at room temperature, the solution was concentrated and the residue was purified on silica, eluting with 20% ethyl acetate in hexane, to give S-methyl—N—[4-(phenoxy)benzenesulfonyl]-D-penicillamine methyl ester as a white solid in 87% yield: $^1$H NMR ($CDCl_3$) δ 1.31 (s, 3H), 1.37 (s, 3H), 1.96 (s,3H), 3.48 (s, 3H), 3.79 (d, 1H, J=9 Hz), 5.34 (d, 1H, J=10 Hz), 6.99–7.79 (m, 9H); FAB HRMS: expected (M+Na)=432.0915, found (M+Na)=432.0907.
Prepared in a similar manner was the following:

Example 6(b)
S-Methyl—N—[4-(4-chlorophenoxy)benzenesulfonyl]-D-penicillamine {III-A, W=$CH_3$S, Z=Cl}
mp 203° C. (decomp); $^1$H NMR ($CDCl_3$) d 1.21 (s, 3H), 1.25 (s, 3H), 1.88 (s, 3H), 3.75–3.84 (m, 1H), 6.91–7.95 (m, 9H); FAB HRMS: expected (M+Cs)$^+$=561.9526. Found (M+Cs)$^+$=561.9538.

Example 7
S—[2-(Methoxycarbonyl)ethyl]—N—[4-(4-fluorophenoxy)benzenesulfonyl]-D-penicillamine {III-A, W=$EtO_2C(CH_2)_2$S, Z=F}

To a 0° C. solution of N-[4-(4-fluorophenoxy) benzenesulfonyl]—S—[2-(methoxycarbonyl)ethyl]-D-penicillamine allyl ester (0.36 g, 0.687 mmol) in 5 mL of ethyl acetate was added N-methylaniline followed by Pd(PPh$_3$)$_4$ (16 mg, 0.014 mmol). After 3 hours, the solution was concentrated, and the residue was purified by chromatography on silica gel, eluting first with 1:1 ethyl acetate-:hexane and then with 10% methanol in dichloromethane to give N-[4-(4-fluorophenoxy)benzenesulfonyl]—S—[2-(methoxycarbonyl)ethyl]-D-penicillamine as a white solid in 89% yield: mp 123–124° C.; $^1$H—NMR(CDCl$_3$) δ 1.27 (s, 3H), 1.35 (s, 3H), 2.40–2.82 (m, 4H), 3.71 (s, 3H), 3.94 (d, 1H, J=11 Hz), 5.60 (d, 1H, J=11 Hz), 6.93–7.82 (m, 8H); FAB HRMS: expected (M+Cs)=618.0033. Found (M+Cs)=618.0038

The starting material was prepared as follows:
(i) N-(tert-Butoxycarbonyl)—S—[2-(methoxycarbonyl)ethyl]-D-penicillamine allyl ester To a suspension of D-penicillamine (10.0 g., 67.02 mmol) in methanol (100 mL) at 0° C. was added 14.5 mL (67 mmol) of a 25 wt % solution of sodium in methanol dropwise. After 15 minutes, methyl acrylate (6.35 mL, 70 mmol) was added dropwise, and the solution was allowed to warm to room temperature overnight. Removal of the solvent by rotary evaporation provided a white solid, which was dissolved in 50% aqueous (100 mL). To the resulting solution was added triethylamine (14 mL, 100 mmol), followed by di-t-butyldicarbonate (16.05 g., 73.6 mmol). After stirring for 12 hours at room temperature, the mixture was concentrated to remove most of the THF, and the resulting aqueous solution was acidified with acetic acid and then extracted with ethyl acetate. The organic layer was washed with brine, dried over magnesium sulfate, and concentrated. The residue was dissolved in THF (75 mL) and DBU (10.2 mL, 68.2 mmol) added, followed by addition of allyl bromide (6.14 mL, 71.0 mmol). The solution was stirred at room temperature for 5 hours, and then the solvent was removed by concentration under reduced pressure. The residue was purified on silica gel, eluting with 5% to 10% to 20% ethyl acetate in hexane, to provide N-(tert-butoxycarbonyl)—S—[2-(methoxycarbonyl)ethyl]-D-penicillamine allyl ester as a colorless oil in 44% overall yield: $^1$H—NMR (CDCl$_3$) δ 1.36 (s, 3H), 1.38 (s, 3H), 1.44 (s, 9H), 2.52–2.57 (t, 2H, J=8 Hz), 2.75–2.82 (m, 2H), 3.69 (s, 3H), 4.32–4.35 (m, 1H), 4.62–4.64 (m, 2H), 5.27–5.39 (m, 3H), 5.85–6.00 (m, 1H); FAB HRMS: expected (M+Cs)=508.0770, found (M+Cs)=508.0750.

(ii) S—[2-(Methoxycarbonyl)ethyl]-D-penicillamine allyl ester, trifluoroacetate salt.

To a solution of N-(tert-butoxycarbonyl)—S—[2-(methoxycarbonyl)ethyl]-D-penicillamine ally] ester (2.00 g., 5.51 mmol) in dichloromethane (25 mL) at 0° C. was added trifluoroacetic acid (6.7 mL) added. After 10 minutes, the solution was allowed to warm to room temperature. After 2.5 hours, the solution was concentrated and then azeotroped with benzene to give S—[2-(methoxycarbonyl)ethyl]-D-penicillamine allyl ester as a trifluoroacetate salt in 95% yield: $^1$H—NMR (CDCl$_3$) δ 1.37 (s, 3H), 1.59 (s, 3H), 2.54–2.87 (2m, 4H), 3.71 (s, 3H), 4.13 (s, 1H), 4.69–4.74 (m, 2H), 5.31 (d, 1H, J=9.5 Hz), 5.39 (d, 1H, J=17.3 Hz), 5.88–5.97 (m, 1H); FAB HRMS:
expected (M+H)=276.1270, found (M+H)=276.1263.
(iii) N-[4-(4-Fluorophenoxy)benzenesulfonyl]—S—[2-(methoxycarbonyl)ethyl]-D-penicillamine allyl ester To a solution of S—[2-(methoxycarbonyl)ethyl]-D-penicillamine allyl ester, trifluoroacetate salt (0.500 g., 1.29 mmol) in dichloromethane (3 mL) at 0° C. was added DBU (0.425 mL, 2.84 mmol) followed by 4-(4-[fluorophenoxy])phenyl sulfonyl chloride(0.438 g., 1.74 mmol). The solution was stirred at 0° C. for 10 minutes and then was allowed to warm to room temperature. After 15 hours, the solution was concentrated, and the residue was purified on silica eluting with 10→25% ethyl acetate in hexane to give N-[4-(4-fluorophenoxy)benzenesulfonyl]—S—[2-(methoxycarbonyl)ethyl]-D-penicillamine allyl ester as a white solid in 66% yield: $^1$H NMR (CDCl$_3$) δ 1.36 (s, 3H), 1.40 (s, 3H), 2.47–2.53 (m,2H), 2.72–2.76 (m, 2H), 3.70 (s, 3H), 3.83 (d, 1H, J=10 Hz), 4.29–4.42 (m, 2H), 5.22 (d, 1H, J=5 Hz), 5.27 (d, 1H J=12 Hz), 5.54 (d, 1H, J=10 Hz), 5.68–5.78 (m,1H), 6.95–7.79 (m, 8H); FAB HRMS: expected (M+Cs)=658.0346, found (M+Cs)=658.0370.

Example 8
Preparation of Compounds of Formula III-A

Example 8(a)
S—[2-Hydroxyethyl]—N—[4-(4-fluorophenoxy)benzenesulfonyl]-D-penicillamine {III-A, W=HO(CH$_2$)$_2$S, Z=F}

Deprotection of S—[2-hydroxyethyl]—N—[4-(4-fluorophenoxy)benzenesulfonyl]-D-penicillamine allyl ester was carried in the same manner as in example 7. Purification on silica, eluting with 10% methanol in dichloromethane provided S—[2-hydroxyethyl]—N—[4-(4-fluorophenoxy)benzenesulfonyl]-D-penicillamine as a white solid in 61% yield: mp 198–200 (decomp); $^1$H—NMR (MeOD) δ 1.36 (s, 3H), 1.40 (s, 3H), 2.58–2.74 (m, 2H), 3.60 (t, 2H, J=7 Hz), 3.66 (s, 1H), 7.04–7.88 (m, 8H).
Anal. calc. for C$_{19}$H$_{22}$FNO$_6$S$_2$•0.5CH$_2$C$_2$: C, 48.19; H, 4.77; N, 2.88. Found: C, 48.44; H, 4.71; N, 2.93.
The starting material was prepared as follows:
(i) N-[4-(4-fluorophenoxy)benzenesulfonyl]-D-penicillamine allyl ester.

To a stirred solution of N-[4-(4-fluorophenoxy)benzenesulfonyl]—S—[2-(methoxycarbonyl)ethyl]-D-penicillamine allyl ester (0.100 g., 0.19 mmol) in DMSO(1 ml.) at room temperature was added sodium thiomethoxide (0.053 g., 0.762 mmol). After 3.5 hours, the reaction was then acidified with 1N aqueous sodium bisulfate to pH=4 and extracted with ethyl acetate. The organic phase was washed with brine, dried over MgSO4, and concentrated. The residue was purified on silica eluting with 20% ethyl acetate in hexane to give N-[4-(4-fluorophenoxy)benzenesulfonyl]-D-penicillamine allyl ester as a colorless oil in 75% yield. $^1$H—NMR (δ, CDCl$_3$) δ 1.43 (s, 6H), 1.93 (s,1H), 3.82–3.86 (d, 1H, J=11 Hz),4.25–4.38 (m, 2H), 5.23–5.29 (m, 2H), 5.49–5.53 (d, 1H, J=11 Hz), 5.63–5.78 (m,1H), 6.96–7.79 (m, 8H)
(ii) S—[2-Hydroxyethyl]—N—[4-(4-fluorophenoxy)benzenesulfonyl]-D-penicillamine allyl ester.

To a 0° C. solution of N-[4-(4-fluorophenoxy)benzenesulfonyl]-D-penicillamine allyl ester (0.200 g., 0.456 mmol) in DMF (2 mL) was added DBU (0.102 ml., 0.68 mmol), followed by 2-bromoethanol (0.049 ml., 0.68 mmol). After 1 hour at 0° C. and 5 hours at room temperature, the reaction was partitioned between brine and ethyl acetate. The organic layer was washed with brine, dried over Na$_2$SO$_4$, and concentrated. Purification of the residue on silica, eluting with 20% ethyl acetate in hexane followed by 10% methanol/methylene chloride, provided S—[2-hydroxyethyl]—N—[4-(4-fluorophenoxy)benzenesulfonyl]-D-penicillamine allyl ester as a white solid in 72% yield. $^1$H—NMR (CDCl$_3$) δ 1.39 (s, 3H), 1.40 (s, 3H), 2.75–2.80 (m, 2H), 3.67–3.78 (m,2H), 3.87 (d,1H, J=10 Hz), 4.25–4.38 (m,2H), 5.22–5.29 (m,2H), 5.66–5.76

(m,1H), 5.93 (d,1H, J=10 Hz), 6.95–7.77 (m, 8H); FAB HRMS: expected (M+Cs)=616.0240, found (M+Cs)=616.0265

The following was prepared in a similar manner:

Example 8(b)

S—[2-(Aminocarbonyl)ethyl]—N—[4-(4-fluorophenoxy) benzenesulfonyl]-D-penicillamine {III-A, W=$H_2N(O=)C(CH_2)_2S$, Z=F} mp 186–187° C. (decomp); $^1H$—NMR ($CD_3OD$) δ 1.37 (s, 3H), 1.43 (s, 3H), 2.40–2.44 (m, 2H), 2.72–2.91(m, 2H), 3.60 (s, 1H), 7.02–7.87 (m, 8H).

Example 9
Preparation of Compounds of Formula II-A

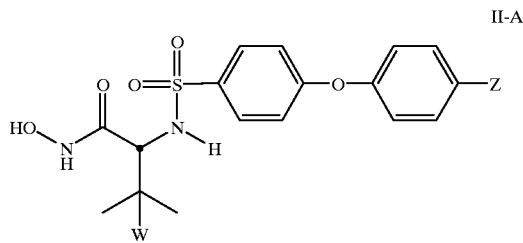

Example 9(a)

2(S)—N—Hydroxy-3-methyl-3-methylsulfanyl-2-[(4-phenoxybenzenesulfonyl)amino]butanamide {II-A, W=$CH_3S$, Z=H}

To a solution of S-methyl—N—[4-(phenoxy) benzenesulfonyl]-D-penicillamine (75 mg., 0.190 mmol) and DMF (0.003 mL., 0.04 mmol) in 1 mL of dichloromethane at −75° C. was added dropwise oxalyl chloride (0.022 mL., 0.247 mmol). The solution was stirred at −75° C. for 15 minutes and then allowed to warm to −25° C. over 45 minutes. The ice bath was then removed, and THF(1 mL.) was added, followed by aqueous hydroxylamine (0.126 mL., 1.90 mmol, 50% sol'n.). The mixture was stirred at room temperature for 2 hours and then partitioned between ethyl acetate and 0.5 N aqueous sodium bisulfate. The organic later was washed with brine, filtered over celite, concentrated, and the residue was azeotroped with benzene. Trituration of the residue with 25% diethyl ether in hexane provided 2(S)—N-hydroxy-3-methyl-3-methylsulfanyl-2-[(4-phenoxybenzenesulfonyl)amino]butanamide as a white solid in 74% yield: mp 161–163° C.; $^1H$ NMR (DMSO-d6) δ 1.25 (s, 3H), 1.28 (s, 3H), 1.97 (s,3H), 3.62–3.66 (m,1H), 7.09–8.91 (m, 10H); FAB HRMS: expected (M+H)=411.1048, found (M+H)=411.1062.

Anal. calc. for $C_{18}H_{22}N_2O_5S_2$: C, 52.66; H, 5.40; N, 6.82. Found: C, 52.58; H, 5.35; N, 6.75.

Prepared in a similar fashion were the following:

Example 9(b)

2(S)—N-hydroxy-3-methyl-3-methylsulfanyl-2-[(4-(4-chlorophenoxy)benzenesulfonyl)amino]butanamide {II-A, W=$CH_3S$, Z=Cl} mp 194–195° C.; $^1H$—NMR (MeOD) δ 1.34 (s, 3H), 1.36 (s,, 3H), 2.01 (s,3H), 3.59 (s,1H), 7.09–7.88 (m, 9H).

Anal. calc. for $C_{18}H_{21}ClN_2O_5S_2$: C, 48.59; H, 4.76; N, 6.30. Found: C, 48.49; H, 4.75; N, 6.21.

Example 9(c)

2(S)—N-hydroxy-3-methyl-3-(5-methylisoxazol-3-yl) methylsulfanyl-2-[(4-(4-fluorophenoxy)benzenesulfonyl) amino]butanamide{II-A, W=(5-methylisoxazol-3-yl)$CH_2S$, Z=F} mp 159° C.; $^1H$ NMR (DMSO-d6) δ 1.3 (s, 3H), 1.33 (s, 3H), 2.42 (s,3H), 3.70–3.83 (m, 3H), 6.20 (s, 1H), 7.09 (d, J=8 Hz, 2H), 7.2–7.4 (2 m, 4H), 7.83 (d, J=7 Hz, 2H), 8.08 (d, J=9 Hz, 1H), 8.94 (s, 1H), 10.67 (s, 1H).

Anal. calc. for $C_{22}H_{24}FN_3O_6S_2$: C, 51.86; H, 4.75; N, 8.25; Found: C, 51.86; H, 4.75; N, 8.25.

Example 9(d)

2(S)—N-hydroxy-3-methyl-3-(5-methylisoxazol-3-yl) methylsulfanyl-2-[(4-(4-bromophenoxy) benzenesulfonyl) amino]butanamide {II-A, W=(5-methylisoxazol-3-yl) $CH_2S$, Z=Br} mp 154° C.; $^1H$—NMR (DMSO-d6) δ 1.31 (s, 3H), 1.33 (s, 3H), 2.42 (s,3H), 3.70–3.82 (m, 3H), 6.22 (s, 1H), 7.10–7.18 (overlapping d, J=9.1, 8.8 Hz, 4H), 7.65 (d, J=8.5 Hz, 2H), 7.85 (d, J=8.5 Hz, 2H), 8.12 (d, J=9.1 Hz, 1H), 10.68 (s, 1H).

Anal. calc. for $C_{22}H_{24}BrN_3O_6S_2$: C, 46.32; H, 4.24; N, 7.37; Found: C, 46.19; H, 4.29; N, 7.18.

Example 9(e)

2(S)—N-hydroxy-3-methyl-3-(pyrid-2-yl)methylsulfanyl-2-[(4-(4-bromophenoxy)benzenesulfonyl)amino] butanamide {II-A, W=(pyrid-2-yl)$CH_2S$, Z=Br} mp 70–73° C.; $^1H$—NMR ($CDCl_3$) δ 1.21 (s,3H), 1.62 (s, 3H), 3.82–3.89 (m, 3H), 4.92 (d, J=5 Hz, 1H), 5.98 (d, J=5 Hz, 1H), 6.85–7.14 (m, 4H), 7.41–7.95 (m, 7H), 8.42 (br s, 1H)

Anal. calc. for $C_{23}H_{24}N_3O_5S_2Br$•0.4 $H_2$•0.5 hexane: C, 49.43, H 4.79, N 7.06.

Found: C, 49.50; H, 4.38; N, 6.90

Example 9(f)

2(S)—N-hydroxy-3-methyl-3-(pyrid-2-yl)methylsulfanyl-2-[(4-(4-iodophenoxy)benzenesulfonyl)amino]butanamide {II-A, W=(pyrid-2-yl)$CH_2S$, Z=I} mp 85–87° C.; $^1H$—NMR ($CDCl_3$) δ 1.55 (s, 3H), 1.63 (s, 3H), 3.84–3.97 (m, 2H), 4.96 (d, J=5.5 Hz, 1H), 5.45 (d, J=5.6 Hz,1H), 5.97 (d, J=4.6 Hz, 1H), 6.83–7.26 (m, 4H), 7.68–7.89 (m, 8H), 11.22 (s, 1H)

Anal.calc. for $C_{23}H_{24}N_3O_5S_2I$: C, 45.30; H, 4.30; N, 6.40. Found: C, 45.33; H, 4.12; N, 6.31.

Example 9(g)

2(S)—N-hydroxy-3-methyl-3-(pyrid-2-yl)methylsulfanyl-2-[(4-(4-methylphenoxy)benzenesulfonyl)amino] butanamide {II-A, W=(pyrid-2-yl)$CH_2S$, Z=$CH_3$} mp 105–108° C.; $^1H$—NMR ($CDCl_3$) δ 1.54 (s, 3H), 1.68 (s, 3H), 2.40 (s, 3H), 3.85–4.01 (m, 3H), 4.95 (d, J=6.0 Hz, 1H), 5.45 (d, J=5.5 Hz, 1H), 5.89 (d, J=6.2 Hz, 1H), 6.98–7.03 (m, 4H), 7.18–7.22 (m, 2H), 7.26–7.86 (m, 4H), 8.47 (d, 4.6 Hz, 2H)

Anal. calc. for $C_{24}H_{27}N_3O_5S_2$•0.1 hexane•1.1AcOH: C, 55.64; H, 5.66; N, 7.35 Found: C, 55.62; H, 5.78; N, 7.38

Example 9(h)

2(S)—N-hydroxy-3-methyl-3-(pyrid-2-yl)methylsulfanyl-2-[(4-(4-fluorophenoxy)benzenesulfonyl)amino] butanamide {II-A, W=(pyrid-2-yl)$CH_2S$, Z=F} mp 66–69° C.; $^1H$—NMR ($CDCl_3$) δ 1.23 (s, 6H), 3.38 (m, 2H), 4.89–4.91 (d, J=7.5 Hz, 1H), 5.58–5.59 (d, J=10.2 Hz,1H), 5.98–6.01 (d, J=7.5 Hz, 1H), 6.97–7.11 (m, 4H), 7.58–8.13 (m, 6H), 8.41 (s, 2H).

Anal. calc. for $C_{23}H_{24}N_3O_5S_2F$•0.2 $H_2O$ •0.2 hexane: C, 55.96; H, 5.52; N, 7.77.

Found: C, 55.90; H, 5.47; N, 7.67.

Example 9(i)

2(S)—N-hydroxy-3-methyl-3-benzylsulfanyl-2-[(4-phenoxybenzenesulfonyl)amino]butanamide {II-A, W=$PhCH_2S$, Z=H} mp 35–37° C.; $^1$H—NMR (CDCl$_3$) δ 1.21 (s, 3H); 1.61 (s, 3H), 3.62–3.82 (m, 2H), 6.98–7.04 (m, 6H), 7.21–7.54 (m, 6H), 7.89–7.91 (m, 2H).
Anal. calc. for C$_{24}$H$_{26}$N$_2$O$_5$S$_2$•0.65H$_2$O•0.2NH$_3$: C, 57.45; H, 5.61; N, 6.14.
Found: C, 57.42; H, 5.59; N, 6.11

Example 9(j)
2(S)—N-hydroxy-3-methyl-3-(t-butoxycarbonyl)methylsulfanyl-2-[(4-(4-fluorophenoxy)benzenesulfonyl)amino]butanamide {II-A, W=t-BuO$_2$CCH$_2$S, Z=F}
mp 138° C.; $^1$H—NMR (DMSO-d6) δ 1.28 (s, 6H), 1.45 (s, 9H), 3.38 (s, 1H), 3.67 (d, J=9.6 Hz, 1H), 7.09 (d, J=8.8 Hz, 2H), 7.20–7.36 (2m, 4H), 7.81 (d, J=8.8 Hz, 2H), 8.02 (d, J=9.9 Hz, 1H), 8.90 (s, 1H), 10.60 (s, 1H).
Anal. calc. for C$_{23}$H$_{29}$FN$_2$O$_7$S$_2$: C, 52.26; H, 5.53; N, 5.30.
Found: C, 52.21; H, 5.54; N, 5.21.

Example 9(k)
2(S)—N-hydroxy-3,3-dimethyl-2-[(4-phenoxybenzenesulfonyl)-amino]butanamide {II-A, W=CH$_3$, Z=H}
mp 129–132° C.; $^1$H—NMR (CDCl$_3$) δ 0.92 (s, 9H), 3.32 (s, 1H), 5.60 (br, 1H), 6.99–7.18 (m, 4H), 7.21–7.42 (m, 4H), 7.77 (d, J=9.0 Hz, 2H).
Anal. calc. for C$_{18}$H$_{22}$N$_2$O$_5$•0.3 H$_2$O: C, 56.32; H, 5.93; N, 7.30; Found: C, 56.31; H, 6.03; N, 7.68

Example 9(l)
2(S)—N-hydroxy-3,3-dimethyl-2-[(4-(4-fluorophenoxy)benzenesulfonyl)-amino]butanamide {II-A, W=CH$_3$, Z=F}
mp 122–125° C.; $^1$H—NMR (CDCl$_3$) δ 0.98 (s, 9H), 3.29 (d, J=9.6 Hz,1H), 5.60 (d, J=10.5 Hz, 1H), 6.97–7.09 (m, 6H), 7.77 (d, J=8.5 Hz, 2H).
Anal. calc. for C$_{18}$H$_{21}$FN$_2$O$_5$S: C, 54.53; H, 5.34; N, 7.07
Found: C, 54.43; H, 5.33; N, 7.13

Example 9(m)
2(S)—N-hydroxy-3,3-dimethyl-2-[(4-(4-chlorophenoxy)benzenesulfonyl)amino]butanamide {II-A, W=CH$_3$, Z=Cl}
mp 164–165° C.; $^1$H—NMR(CD$_3$OD): 1.00 (s, 9 H), 3.30 (s, 1H), 7.08–7.86 (m, 8H); FAB HRMS: expected (M+H)= 413.0938, Found (M+H)=413.0951.
Anal. calc. for C$_{18}$H$_{21}$ClN$_2$O$_5$S: C, 52.36; H, 5.13; N, 6.79
Found: C, 52.21; H, 5.23; N, 6.66.

Example 9(n)
2(S)—N-hydroxy-3-methyl-3-(1-methyl-1H-imidazol-2-yl)-methylsulfanyl-2-[(4-(4-bromophenoxy)benzenesulfonyl)amino]butanamide {II-A, W={1-methyl-1H-imidazol-2-yl)CH$_2$S, Z=Br}: $^1$H NMR (DMSO): δ 1,23 (s, 3H), 1.28 (s, 3H), 3.32 (s, 3H), 3.67 (d, 1H, J=9.9 Hz), 3.80 (d, 1H, J=13.6 Hz, AB), 3.90 (d, 1H, J=13.6 Hz, AB), 6.77 (s, 1H), 7.04–7.12 (m, 5H), 7.59 (d, 2H, J=9.0 Hz), 7.76 (d, 2H, J=8.7 Hz), 8.05 (d, 1H, J=9.9 Hz), 9.10 (s, 1H), 10.96 (s, 1H).
ESIMS Calcd for C$_{22}$H$_{25}$BrN$_4$O$_5$S$_2$: 569/571. Found: 569/571.
Examples 9(o) through 9(s) may be prepared in a similar fashion:

Example 9(o)
2(S)—N-hydroxy-3-methyl-3-(1-methyl-1H-imidazol-2-yl)methylsulfanyl-2-[(4-(4-bromophenoxy)benzenesulfonyl)amino]butanamide {II-A, W=(1-methyl-1H-imidazol-2-yl)CH$_2$S, Z=Br}

Example 9(p)
2(S)—N-hydroxy-3-methyl-3-(1H-imidazol-4-yl)methylsulfanyl-2-[(4-(4-bromophenoxy)benzenesulfonyl)amino]butanamide {II-A, W=(1H-imidazol-4-yl)CH$_2$S, Z=Br}

Example 9(q)
2(S)—N-hydroxy-3-methyl-3-(1-methyl-1H-imidazol-4-yl)methylsulfanyl-2-[(4-(4-bromophenoxy)benzenesulfonyl)amino]butanamide {II-A, W=(1-methyl-1H-imidazol-4-yl)CH$_2$S, Z=Br}

Example 9(r)
2(S)—N-hydroxy-3-methyl-3-(4-methyl-4H-[1,2,4]-triazol-3-yl) methylsulfanyl-2-[(4-(4-bromophenoxy)benzenesulfonyl)amino]butanamide {II-A, W=(4-methyl-4H-[1,2,4]-triazol-3-yl)CH$_2$S, Z=Br}

Example 9(s)
2(S)—N-hydroxy-3-methyl-3-(1-methyl-4H-[1,2,4]-triazol-3-yl) methylsulfanyl-2-[(4-(4-bromophenoxy)benzenesulfonyl)amino]butanamide {II-A, W=(1-methyl-4H-[1,2,4]-triazol-3-yl)CH$_2$S, Z=Br}
Examples 10(a), 10(b), and 10(c) were prepared in a manner similar to that described in Example 9(a).

Example 10(a)
2(S)—N-hydroxy-3-methyl-3-(5-methylisoxazol-3-yl)methylsulfanyl-2-[(4-(pyrid-4-yloxy)benzenesulfonyl)amino]butanamide

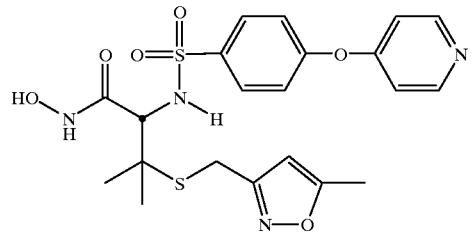

Prepared according to the procedure described in Example 9(a): mp 71–72° C. $^1$H NMR (CD$_3$OD) δ 1.4 (s, 3H), 1.6 (s, 3H), 2.4 (s, 3H), 3.68 (s, 1H), 3.78 (d, 2H, J=10.6 Hz), 6.08 (s, 1H), 7.08 (d, 2H, J=5.0 Hz), 7.26 (d, 2H, J=9.0 Hz), 7.94 (d, 2H, J=9.0 Hz), 8.44 (d, 2H, J=6.2 Hz).
Anal. Calcd for C$_{21}$H$_{24}$O$_6$N$_4$S$_2$•0.5 H$_2$O•1.1 HOAc: C, 49.09; H, 5.22; N, 9.87; S, 11.30.
Found: C, 49.33; H, 5.23; N, 9.69; S, 10.94.

Example 10(b)
2(S)—N-hydroxy-3-methyl-3-(5-methylisoxazol-3-yl)methylsulfanyl-2-[(4-{(pyrid-4-yl)sulfanyl}benzenesulfonyl)amino]butanamide

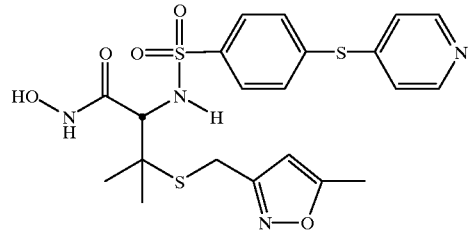

$^1$H NMR (acetone-d$_6$): δ 1.36 (s, 3H), 1.40 (s, 3H), 2.38 (s, 2H), 3.75 (d, 1H, J=13.4 Hz), 3.83 (d, 1H, J=13.4 Hz), 3.88

(s, 1H), 6.18 (s, 1H), 7.10–7.22 (m, 2H), 7.68 (d, 2H, J=7.4 Hz), 7.94 (d, 2H, J=7.4 Hz), 8.35–8.50 (m, 2H). IR: 3222, 1670,1578, 1332, 1165 cm$^{-1}$. HR FABMS: Calcd for $C_{21}H_{24}N_4O_5S_3Cs$ (M+Cs$^+$): 640.9963. Found: 640.9988. Anal. Calcd for $C_{21}H_{24}N_4O_5S_3$•0.1 $C_7H_{16}$•0.3 CHCl$_3$: C, 47.66; H, 4.71; N, 10.10; S, 17.35. Found: C, 47.67; H, 4.69; N, 10.05; S, 17.42.

Example 10(c)
2(S)—N-hydroxy-3,3-dimethyl-2-[4-(pyrid-2-yl)oxybenzenesulfonyl)amino]butanamide

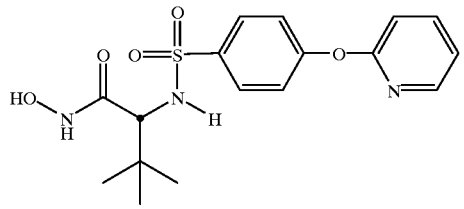

mp 186–187° C.; $^1$H NMR (CD$_3$OD) δ 1.01 (s, 9H), 3.30 (s, 1H), 7.15–8.22 (m, 8 H); FAB HRMS: expected (M+Cs)= 512.0256, Found (M+Cs)=512.0267

Example 11.2
(S), S(R/S)—N-hydroxy-3-methyl-3-(pyrid-2-yl)methylsulfinyl-2-[(4-(4-bromophenoxy)benzenesulfonyl)amino]butanamide

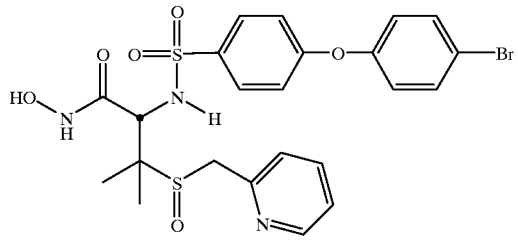

To a 0° C. solution of 2(S)—N-hydroxy-3-methyl-3-(pyrid-2-yl)methylsulfanyl-2-[(4-(4-bromophenoxy)benzenesulfonyl)amino]butanamide (57 mg) in dichloromethane (1 mL) was added 17 mg of m-chloroperbenzoic acid. The mixture was allowed to warm slowly to room temperature overnight, and then partitioned between ethyl acetate and sat. aq. sodium bicarbonate. The organic layer was washed with brine, dried over sodium sulfate, and concentrated. The residue was purified by chromatography on silica gel, eluting first with ethyl acetate and then with 10% methanol in dichloromethane. The product fractions were concentrated and then triturated with t-butyl methyl ether/hexane to give 23.8 mg (41%) of 2(S), S(R/S)—N-hydroxy-3-methyl-3-(pyrid-2-yl) methylsulfinyl-2-[(4-(4-bromophenoxy)benzenesulfonyl)amino]butanamide as a white solid: mp 103–105° C.; $^1$H—NMR (CDCl$_3$) δ 1.21 (s, 3H), 1.25 (s, 3H), 4.09–4.14 (m,3H), 4.65 (d, J=6.0 Hz, 1H), 5.62 (d, 1H), 6.02 (br 1H), 6.91–7.00 (m, 5H), 7.40–7.47 (m, 6H), 8.52 (s, 2H), 10.02 (s, 1H).

Example 12
2(S)—N-hydroxy-3-methyl-3-(carboxymethyl)sulfanyl-2-[(4-(4-fluorophenoxy)benzenesulfonyl)amino]butanamide To a solution of 59.5 mg (0.113 mmol) of 2(S)—N-hydroxy-3-methyl-3-(t-

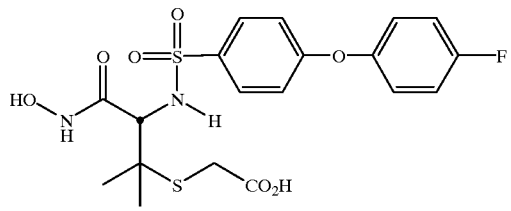

butoxycarbonyl)methylsulfanyl-2-[(4-(4-fluorophenoxy)benzenesulfonyl)amino] butanamide (Example 9(j)) in dichloromethane (1.1 mL) at 20° C. was added trifluoroacetic acid (0.26 mL). After 16 hours, an additional 0.1 mL of trifluoroacetic acid was added. After an additional 6 hours, the reaction was diluted with 5 mL of benzene and then concentrated. The residue was purified by chromatography on silica gel, eluting with 5% methanol in chloroform containing 0.1% acetic acid, to give 28.9 mg (54%) of 2(S)—N-hydroxy-3-methyl-3-(carboxymethyl)sulfanyl-2-[(4-(4 -fluorophenoxy)benzenesulfonyl)amino]butanamide as an off-white solid: mp 180° C.; $^1$H—NMR (DMSO-d6) δ 1.19 (s, 3H), 1.25 (s, 3H), 3.03 (d, J=16.9 Hz, 1H), 3.13 (d, J=16.9 Hz, 1H), 3.85–4.00 (b rs, 1H), 7.08 (d, J=8.8 Hz, 2H), 7.2–7.36 (2m, 4H), 7.77 (d, J=8.8 Hz, 2H), 8.30–8.50 (br s, 1H), 8.70–8.90 (br s, 1H), 11.90–12.20 (br s, 1H).
Anal. calc. for $C_{19}H_{21}FN_2O_7S_2$•0.5 $H_2O$•0.5 CHCl$_3$: C, 43.28; H, 4.19; N, 5.17. Found: C, 43.36; H, 4.40; N, 4.91.

The results obtained during biological testing of some preferred embodiments of the inventive compounds are described below.

BIOLOGICAL DATA
Isolation of MMP's for Assays

The catalytic domain of human collagenase-1 was expressed as a fusion protein with ubiquitin in *E. coli* (see Gehring, E. R., *J Biol. Chem.*, 1995, 270, 22507). After purification of the fusion protein, the fibroblast collagenase-1 catalytic domain (HFC) was released either by treatment with purified, active stromelysin-1 (1:50 w/w ratio), which generated nearly 100% N-terminal Phe1, or by autoprocessing the concentrated collagenase-1 fusion and then incubating at 37° C. for 1 hour. Final purification was completed using zinc chelate chromatography.

The propeptide and catalytic domain of human collagenase-3 (Coll3) was expressed in *E. coli* as an N-terminal fusion protein with ubiquitin. After purification of the fusion from inclusion bodies, the catalytic domain was liberated by treatment with 2 mM APMA at room temperature overnight. Final purification was completed using copper chelate chromatography.

The catalytic domain of human stromelysin (Sln) was obtained by expression and purification of a C-terminally truncated prostromelysin-1 from *E. coli* host BL21 (see Marcy et al. *Biochem.*, 1991, 30, 6476). The subsequent activation of the mature form (Sln) was completed with 2 mM APMA for 1 hour at 37° C., followed by separation using a sizing column.

Human matrilysin (Matr) was expressed in *E. coli* as a fusion protein with ubiquitin. After purification of the matrilysin/ubiquitin fusion from inclusion bodies, the catalytic domain was liberated by treatment with 2 mM APMA at 37° C. for 2 hours. Final purification was complete using copper chelate chromatography.

The catalytic and fibronectin-like portion of human progelatinase A (GelA) was expressed as a fusion protein with ubiquitin in *E. Coli*. Assays were carried out on autocatalytically activated material.

Compounds of Formula I exhibited the ability to inhibit MMPs when tested in the following assay.

In Vitro Assay Procedure

Assays were performed in assay buffer (50 mM Tricine pH 7.5, 200 mM sodium chloride, 10 mM calcium chloride, 0.5 mM zinc acetate containing 2% dimethyl sulfoxide (DMSO)) once the substrate and inhibitor were diluted into it. Stock solutions of inhibitors were prepared in 100% DMSO. Stock solutions of the substrate were prepared in 100% DMSO at a concentration of 6 mM.

The assay method was based on the hydrolysis of MCA-Pro-Leu-Gly-Leu-DPA-Ala-Arg-$NH_2$ (American Peptide Co.) at 37° C. (see Knight, C. G. et al., *FEBS*, 1992, 296, 263–266). The fluorescence changes were monitored with a Perkin-Elmer LS-50B fluorimeter using an excitation wavelength of 328 nm and an emission wavelength of 393 nm. The substrate concentration used in the assays was 10 μM. The inhibitor was diluted into the assays from a solution in 100% DMSO, and controls substituted an equal volume of DMSO so that the final DMSO concentration from inhibitor and substrate dilution in all assays was 2%. The concentration of enzyme in the assay ranged from 60 pM for gelatinase A to 1.5 nM for stromelysin and is a function of the enzymes respective $k_{cat}/K_m$ for the MCA peptide substrate. Proper determination of steady-state rates of substrate cleavage required assay lengths of 60 minutes to allow for complete equilibration of the enzyme-inhibitor complex.

The $K_m$ for the MCA peptide substrate with the matrix metalloproteinases is quite high and exceeds its solubility under assay conditions. Consequently, the apparent $K_i$ ($K_{i,app}$) was determined to describe the strength of inhibition. However, in this case, $K_{i,app}$ would be essentially equal to $K_i$ since [S]<<$K_m$. For the determination of $K_{i,app}$, the concentration of the inhibitor was varied at a constant and low concentration of substrate and the steady-state rates of fluorescence change determined. In most cases absorptive quench due to the presence of ligand was not observed. For slow-binding inhibitors, onset of inhibition curves were collected for at least 45 minutes so that equilibrium was established. Steady-state rates of fluorescence change were obtained by fitting a curve to an equation for a single exponential decay containing a linear phase. The fitted value of the linear phase was taken as the steady-state rate. The steady-state rates were fitted to the Michaelis equation describing competitive inhibition by non-linear methods. Data resulting from tight-binding inhibition was analyzed, and $K_{i,app}$ determined by fitting the data to the tight-binding equation of Morrison (*Biochem. Biophys. Acta*, vol. 185, pp. 269–286 (1969)) by non-linear methods.

The results of the above-described tests are presented below in Table 1. All Ki values are in nM units.

TABLE 1

| Example | Structure | Sin Ki | Matri Ki | HFC Ki | Gel A Ki | Coll3 Ki |
|---|---|---|---|---|---|---|
| 3a | 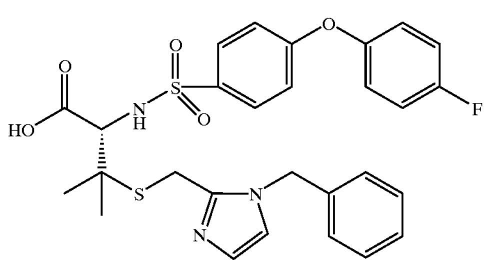 | 1300 | | | 11 | 200 |
| 3b | 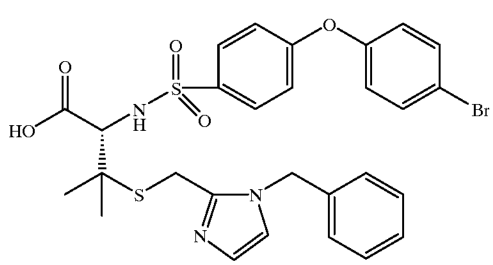 | 558 | | | 1.8 | 108 |
| 3c | 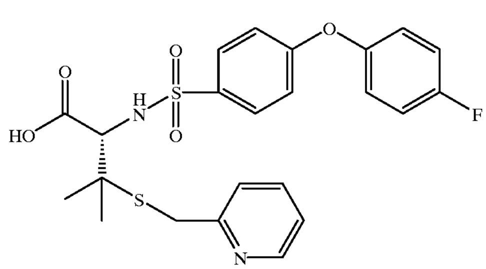 | 2550 | | | 44 | 110 |

TABLE 1-continued
| Example | Structure | Sin Ki | Matri Ki | HFC Ki | Gel A Ki | Coll3 Ki |
|---------|-----------|--------|----------|--------|----------|----------|
| 3d | 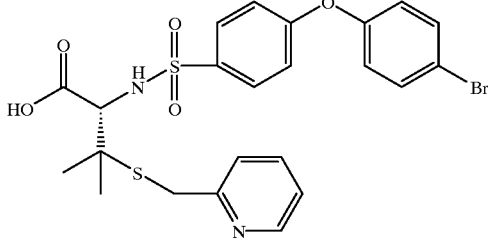 | 1500 | 75000 | 34000 | 7 | 178 |
| 3e | 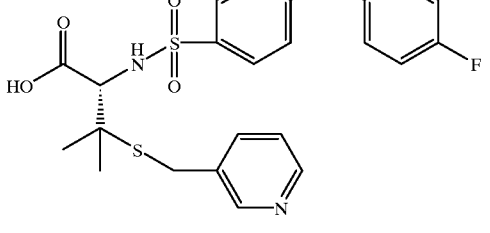 | 6900 | | | 517 | 1100 |
| 3f | 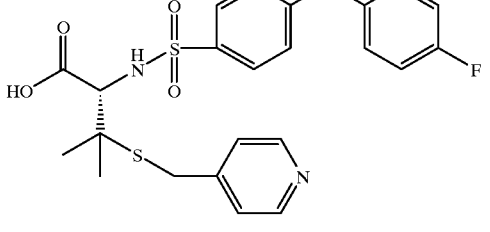 | 6300 | | | 311 | 829 |
| 3g | 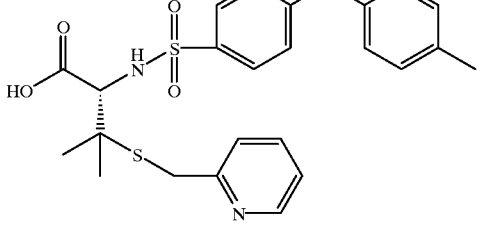 | 1313 | | | 10 | 117 |
| 3h | 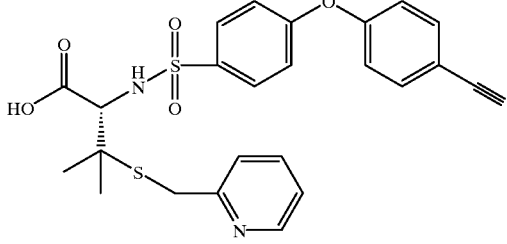 | 8200 | | | 73 | 258 |

TABLE 1-continued

| Example | Structure | Sin Ki | Matri Ki | HFC Ki | Gel A Ki | Coll3 Ki |
|---------|-----------|--------|----------|--------|----------|----------|
| 3i | 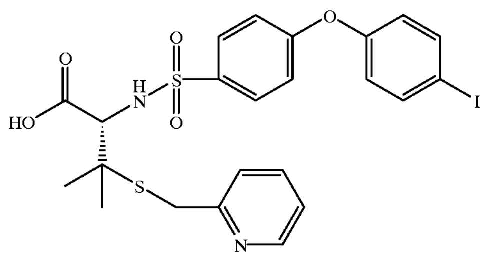 | 1180 | | | 3.3 | 196 |
| 3j | 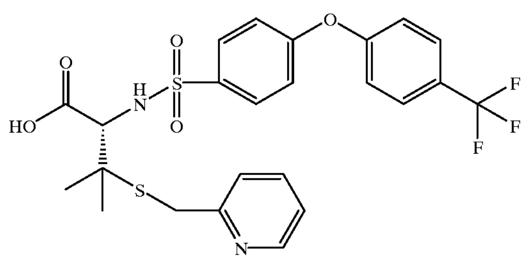 | 2950 | | | 48 | |
| 3k | 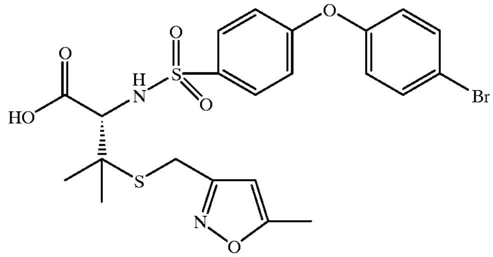 | 2600 | | | 4.2 | 209 |
| 3l | 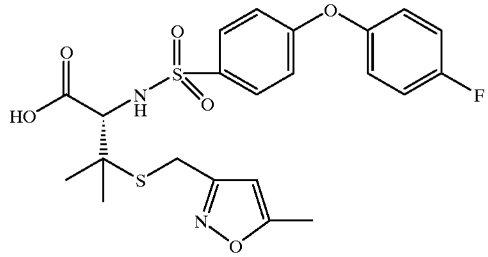 | 5100 | | | 35.3 | 248 |
| 3m | 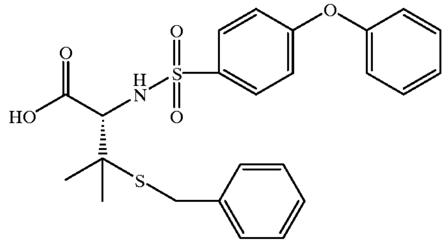 | 1000 | | | 46 | 907 |

TABLE 1-continued

| Example | Structure | Sin Ki | Matri Ki | HFC Ki | Gel A Ki | Coll3 Ki |
|---|---|---|---|---|---|---|
| 3n | 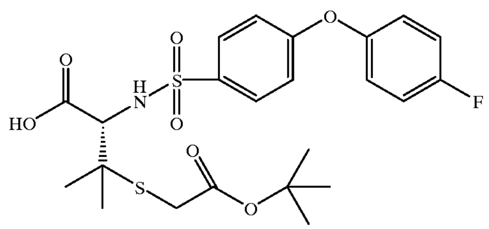 | 5700 | | | 183 | 574 |
| 3o | 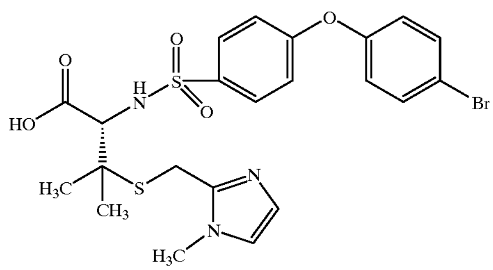 | 2150 | | | 34 | |
| 3p | 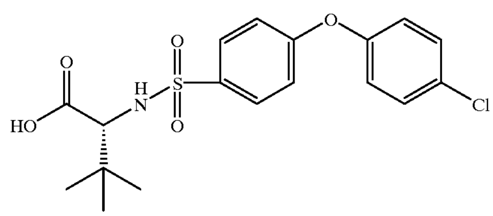 | 9500 | | | 62 | 203 |
| 3q | 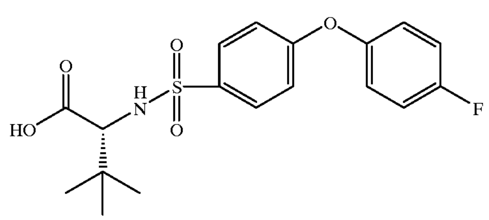 | 14000 | | | 150 | 1180 |
| 3r | 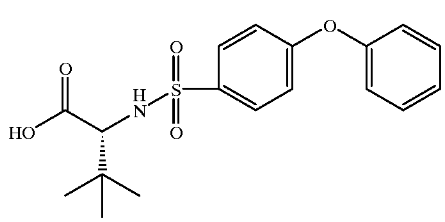 | 12745 | | | 104 | 616 |
| 3s | 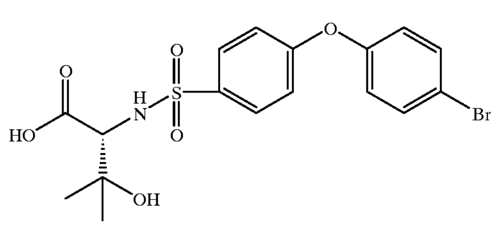 | 348000 | | | 900 | |

TABLE 1-continued

| Example | Structure | Sin Ki | Matri Ki | HFC Ki | Gel A Ki | Coll3 Ki |
|---------|-----------|--------|----------|--------|----------|----------|
| 4a | 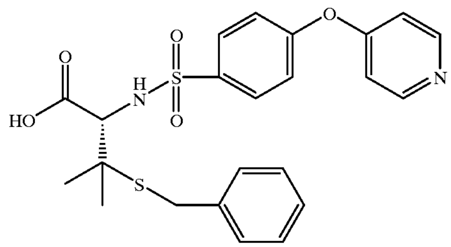 | 7700 | | | 193 | 360 |
| 4b | 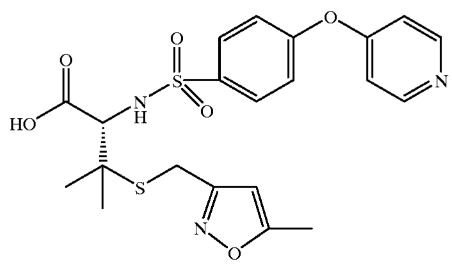 | 751 | | | 27 | |
| 4c | 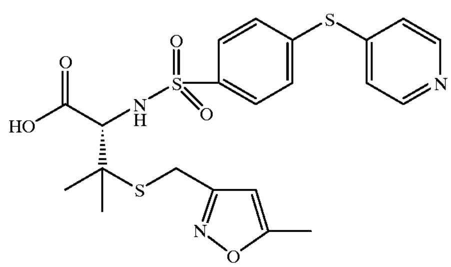 | 97000 | | | 890 | 7000 |
| 4d | 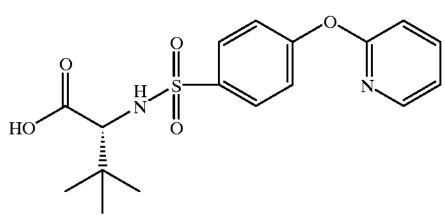 | 274000 | | | 11000 | 27000 |
| 4e | 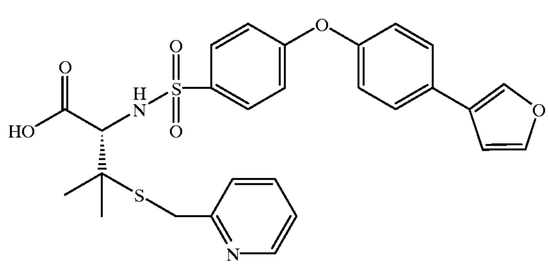 | 680 | | | 7.1 | 153 |
| 5 | 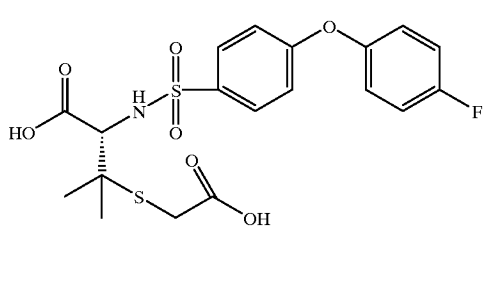 | 27300 | | | 1550 | 1620 |

TABLE 1-continued

| Example | Structure | Sin Ki | Matri Ki | HFC Ki | Gel A Ki | Coll3 Ki |
|---|---|---|---|---|---|---|
| 6a | 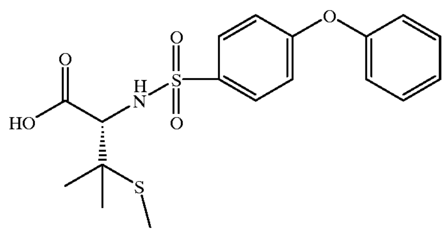 | 4850 | | | 351 | 661 |
| 6b | 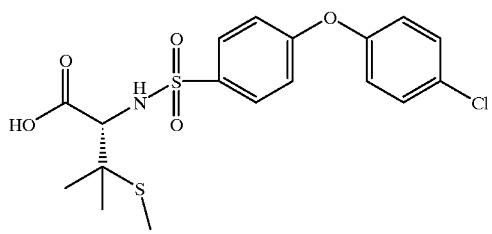 | 17000 | | | 215 | 696 |
| 7 | 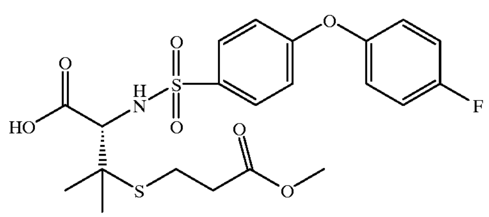 | 10500 | | | 165 | |
| 8a | 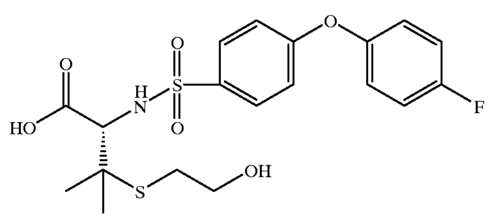 | 12500 | | | 373 | |
| 8b | 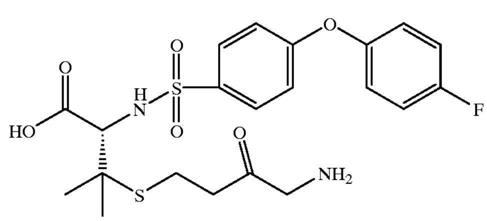 | 5700 | | | 334 | |
| 9a | 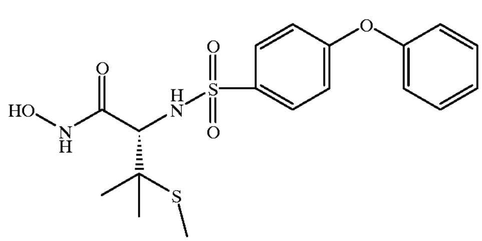 | 2.2 | | | 0.069 | 0.067 |

TABLE 1-continued

| Example | Structure | Sin Ki | Matri Ki | HFC Ki | Gel A Ki | Coll3 Ki |
|---------|-----------|--------|----------|--------|----------|----------|
| 9b | 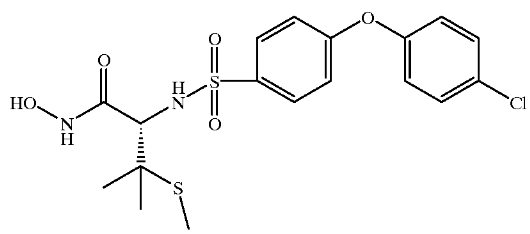 | 1.5 | 115 | 30 | 0.065 | 0.042 |
| 9c | 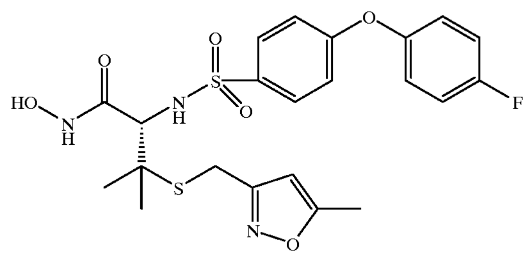 | 0.63 | | | 0.024 | |
| 9d | 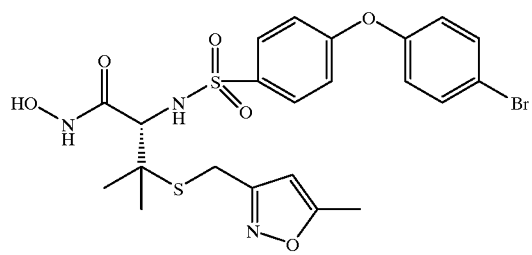 | 0.24 | | | 0.007 | 0.013 |
| 9e | 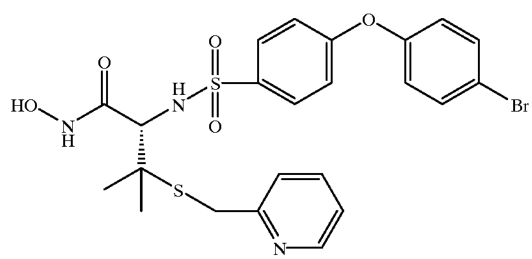 | 0.26 | 7.9 | 4.1 | 0.009 | 0.009 |
| 9f | 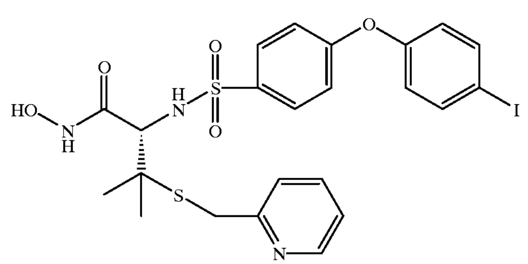 | 0.29 | | | 0.007 | 0.015 |

TABLE 1-continued

| Example | Structure | Sin Ki | Matri Ki | HFC Ki | Gel A Ki | Coll3 Ki |
|---------|-----------|--------|----------|--------|----------|----------|
| 9g | 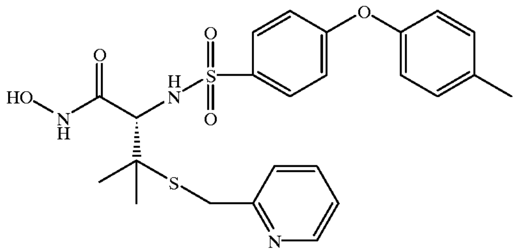 | 0.73 | | | 0.036 | |
| 9h | 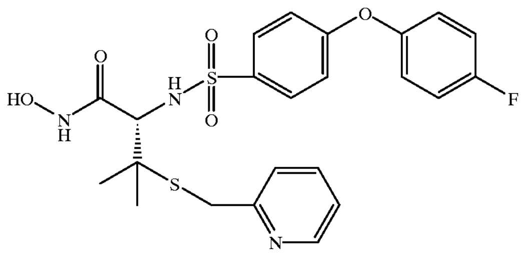 | 0.84 | | 17 | 0.031 | 0.057 |
| 9i | 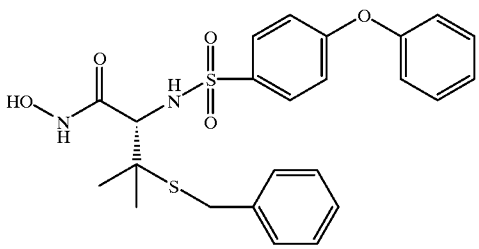 | 1.4 | 26 | 33 | 0.038 | 0.16 |
| 9j | 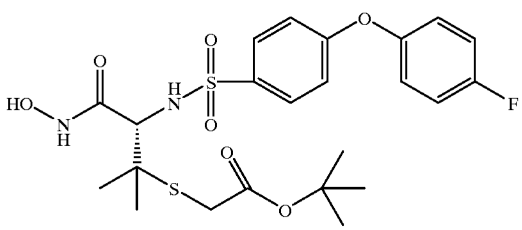 | 1.6 | | 33 | 0.048 | 0.091 |
| 9k | 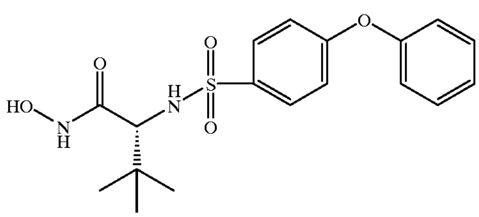 | 4.2 | 376 | 53 | 0.091 | 0.057 |
| 9l | 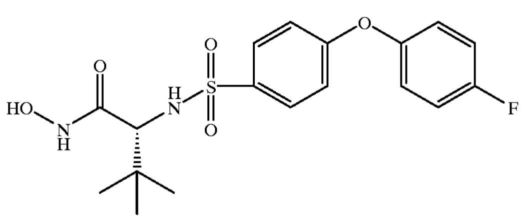 | 1.8 | 120 | 30 | 0.109 | 0.059 |

TABLE 1-continued

| Example | Structure | Sin Ki | Matri Ki | HFC Ki | Gel A Ki | Coll3 Ki |
|---------|-----------|--------|----------|--------|----------|----------|
| 9m | 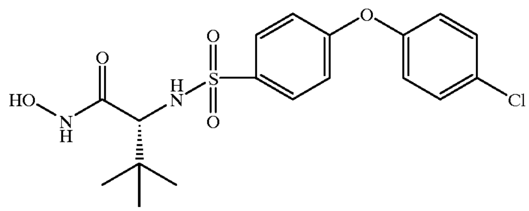 | 1 | 93 | 21 | 0.09 | 0.034 |
| 9n | 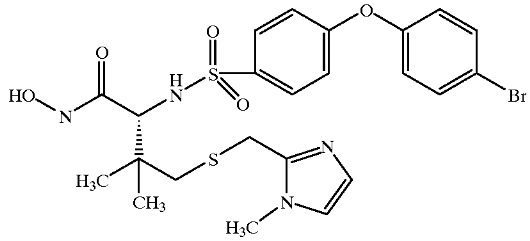 | 0.2 | | | 0.11 | |
| 10a | 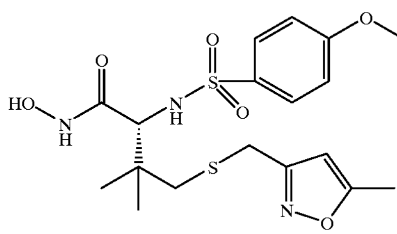 | 11.4 | | | 0.32 | |
| 10b | 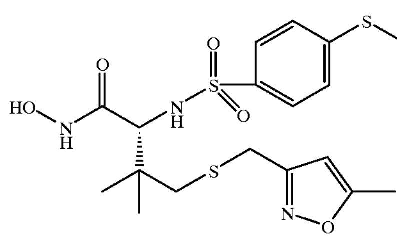 | 38 | | | 0.75 | 1.6 |
| 10c | 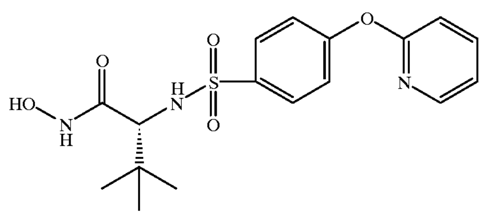 | 71 | 2268 | 960 | 5.1 | 4.6 |
| 11 | 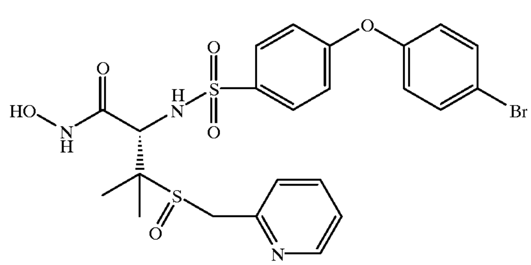 | 1 | | 24 | 0.049 | 0.028 |

TABLE 1-continued

| Example | Structure | Sin Ki | Matri Ki | HFC Ki | Gel A Ki | Coll3 Ki |
|---|---|---|---|---|---|---|
| 12 | 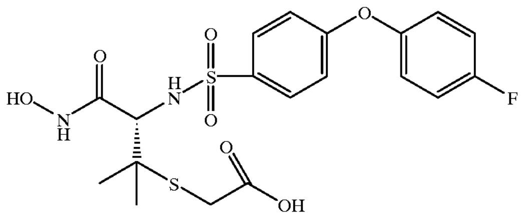 | 5.7 | | | 0.53 | 0.27 |

Example 13

Comparative Example

The compound of Example 9 from WO 95/35276, N-hydroxy-2-(toluene-4-sulfonylamino)acetamide (compound 13 shown below in Table 2), was prepared and its Ki's against gelatinase A and Stromelysin were determined. Table 2 shows these results in comparison to the results obtained for representative preferred compounds from the present invention.

TABLE 2

| COMPOUND NO. | STROMELYSIN Ki (nM) | GELATINASE Kj (nM) |
|---|---|---|
| 13 | 3400 | 3500 |
| 9d | 0.24 | 0.007 |
| 9e | 0.26 | 0.009 |
| 9m | 1.0 | 0.09 |

Thus, the compounds of Examples 9d, 9e, and 9m are 3400 to 500,000 times more potent as inhibitors of stromelysin and gelatinase A than the composition of Example 13, not according to the invention.

We claim:

1. A compound of formula I:

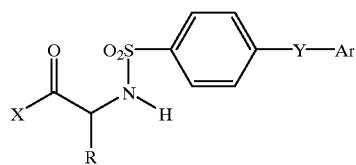

(I)

wherein:
Y is O or S;
Ar is an aryl group or a heteroaryl group;
R is H, an alkyl group, a cycloalkyl group, a heterocycloalkyl group, an aryl group, a heteroaryl group, or —C(O)R$_1$,
  wherein R$_1$ is hydrogen, an alkyl group, a cycloalkyl group, a heterocycloalkyl group, an aryl group, a heteroaryl group, or NR$_2$R$_3$, wherein R$_2$ and R$_3$ independently are hydrogen, an alkyl group, a cycloalkyl group, a heterocycloalkyl group, an aryl group, or a heteroaryl group;
X is —NH—OH or —OH;
or a pharmaceutically acceptable prodrug, salt or solvate thereof.

2. A compound according to claim 1, wherein Ar is an aryl group substituted with a suitable substitutent in the position para to the Y moiety; or a pharmaceutically acceptable prodrug, salt or solvate thereof.

3. A compound according to claim 2, wherein said suitable substituent is a halogen, an alkyl group, an O-alkyl group, an aryl group, a heteroaryl group, or an S-alkyl; or a pharmaceutically acceptable prodrug, salt or solvate thereof.

4. A compound according to claim 1, wherein R is an alkyl group; or a pharmaceutically acceptable prodrug, salt or solvate thereof.

5. A compound according to claim 4, wherein R is the alkyl group —C(CH$_3$)$_2$—S-alkyl, or a pharmaceutically acceptable prodrug, salt or solvate thereof.

6. A compound according to claim 5, wherein R is the alkyl group —C(CH$_3$)$_2$—S—CH$_2$-heteroaryl; or a pharmaceutically acceptable prodrug, salt or solvate thereof.

7. A compound according to claim 1, wherein Y is O.

8. A compound according to claim 1, wherein Y is S.

9. A compound according to claim 1, wherein said compound has the formula Ia:

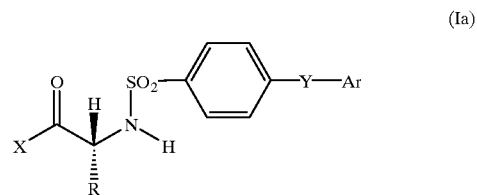

(Ia)

or a pharmaceutically acceptable prodrug, salt or solvate thereof.

10. A compound according to claim 1, wherein said compound is selected from:
2(S)—N-hydroxy-3,3-dimethyl-2-[(4-(4-fluorophenoxy)benzenesulfonyl)-amino]butanamide,
2(S)—N-hydroxy-3,3-dimethyl-2-[(4-(4-chlorophenoxy)benzenesulfonyl)-amino]butanamide,
2(S)—N-hydroxy-3-methyl-3-(pyrid-2-yl)methylsulfanyl-2-[(4-(4-fluorophenoxy)benzenesulfonyl)amino]butanamide,
2(S)—N-hydroxy-3-methyl-3-(pyrid-2-yl)methylsulfanyl-2-[(4-(4-bromophenoxy)-benzenesulfonyl)amino]butanamide,
N-[4-(4-Bromophenoxy)benzenesulfonyl]—S—[(1-benzyl-1H-imidazol-2-yl)methyl]-D-penicillamine,
N-[4-(4-Iodophenoxy)benzenesulfonyl]—S—[(pyrid-2-yl)methyl]-D-penicillamine,
2(S)—N-hydroxy-3-methyl-3-(pyrid-2-yl)methylsulfanyl-2-[(4-(4-iodophenoxy)benzenesulfonyl)amino]butanamide, N-[4-(4-Bromophenoxy)benzenesulfonyl]—S—[(5-methylisoxazol-3-yl)methyl]-D-penicillamine, 2(S)—N-hydroxy-3-methyl-3-(5-methylisoxazol-3-yl)methylsulfanyl-2-[(4-(4-fluorophenoxy)benzenesulfonyl)amino]butanamide, 2(S)—N-hydroxy-3-methyl-3-(5-methylisoxazol-3-yl)methylsulfanyl-2-[(4-(4-bromophenoxy)benzenesulfonyl)amino]butanamide, 2(S)—N-hydroxy-3-methyl-3-(pyrid-2-yl)methylsulfanyl-2-[(4-(4-methylphenoxy)benzenesulfonyl)amino]butanamide, 2(S)—N-hydroxy-3-methyl-3-(5-methylisoxazol-3-yl)methylsulfanyl-2-[(4-(pyrid-4-yloxy)benzenesulfonyl)amino]butanamide, 2(S)—N-hydroxy-3-methyl-3-(5-methylisoxazol-3-yl)methylsulfanyl-2-[(4-{(pyrid-4-yl)sulfanyl}benzenesulfonyl)amino]butanamide, 2(S)—N-hydroxy-3-methyl-3-(1H-imidazol-4-yl)methylsulfanyl-2-[(4-(4-bromophenoxy)benzenesulfonyl)amino]butanamide, 2(S)—N-hydroxy-3-methyl-3-(1-methyl-1H-imidazol-2-yl) methylsulfanyl-2-[(4-(4-bromophenoxy)benzenesulfonyl)amino]butanamide, 2(S)—N-hydroxy-3-methyl-3-(1-methyl-1H-imidazol-4-yl) methylsulfanyl-2-[(4-(4-bromophenoxy)benzenesulfonyl)amino]butanamide, 2(S)—N-hydroxy-3-methyl-3-(4-methyl-4H-[1,2,4]-triazol-3-yl) methylsulfanyl-2-[(4-(4-bromophenoxy)benzenesulfonyl)amino]butanamide, 2(S)—N-hydroxy-3-methyl-3-(1-methyl-4H-[1,2,4]-triazol-3-yl) methylsulfanyl-2-[(4-(4-bromophenoxy)benzenesulfonyl)amino]butanamide, 2(S)—N-hydroxy-3-methyl-3-methylsulfanyl-2-[(4-(4-chlorophenoxy)benzenesulfonyl)amino]butananamide;

and pharmaceutically acceptable prodrugs, salts, and solvates thereof.

11. A pharmaceutical composition comprising:
(a) a therapeutically effective amount of a compound as defined in claim 1 or a pharmaceutically acceptable prodrug, salt or solvate thereof; and
(b) a pharmaceutically acceptable carrier, diluent, vehicle or excipient.

12. A method of treating a mammalian disease condition mediated by metalloproteinase activity which comprises administering to a mammal in need thereof a therapeutically effective amount of a compound as defined in claim 1 or a pharmaceutically acceptable prodrug, salt or solvate thereof.

13. A method according to claim 12, wherein the mammalian disease condition is tumor growth, invasion or metastasis.

14. A method according to claim 12 wherein the mammalian disease condition is osteparthritis, rheumatoid arthritis, osteoporosis, periodontitis, or gingivitis.

15. A method according to claim 12 wherein the mammalian disease condition is chronic dermal wounds, corneal ulceration, or degenerative skin disorders.

16. A method according to claim 12 wherein the mammalian disease condition is multiple sclerosis or stroke.

17. A method according to claim 12 wherein the mammalian disease condition is atherosclerosis, glomerular disease, or Alzheimer's disease.

18. A method according to claim 12 wherein the mammalian disease condition is characterized by unwanted angiogenesis.

19. A method according to claim 12, wherein the mammalian disease condition is diabetic retinopathy, macular degeneration, angiofibromas, or hemangiomas.

20. A method according to claim 12, wherein the mammalian disease condition is mediated by matrix metalloproteinase activity.

21. A method according to claim 12, wherein the mammalian disease condition is mediated by TNF-α convertase activity.

22. A method of inhibiting the activity of at least one metalloproteinase which comprises contacting said at least one metalloproteinase with an effective amount of a compound as defined in claim 1 or a pharmaceutically acceptable prodrug, salt or solvate thereof.

23. A method according to claim 22, wherein said at least one metalloproteinase is a matrix metalloproteinase.

24. A method according to claim 22, wherein said at least one metalloproteinase is a TNF-α convertase.

* * * * *

UNITED STATES PATENT AND TRADEMARK OFFICE
CERTIFICATE OF CORRECTION

PATENT NO. : 5,985,900
DATED       : November 16, 1999
INVENTORS   : STEVEN L. BENDER ET AL.

It is certified that error appears in the above-identified patent and that said Letters Patent is hereby corrected as shown below:

<u>COVER PAGE</u>:
 [56] OTHER PUBLICATIONS,
 After Robinson et al., "Gen-Disubstitution" should read
      --Gem-Disubstitution--.
 [56] FOREIGN PATENT DOCUMENTS,
 "438 223 A1 8/1991" should read --438 223 A1 7/1991--.

<u>COLUMN 15</u>:
 Line 26, "Vil" should read --VIII--.

<u>COLUMN 56</u>:
 Line 11, "osteparthritis" should read --osteoarthritis--.

Signed and Sealed this

Sixteenth Day of January, 2001

Attest:

Q. TODD DICKINSON

*Attesting Officer*    Commissioner of Patents and Trademarks